United States Patent [19]
Festal et al.

[11] Patent Number: 5,219,859
[45] Date of Patent: Jun. 15, 1993

[54] INDOLE DERIVATIVES, PREPARATION PROCESSES AND MEDICINAL PRODUCTS CONTAINING THEM

[75] Inventors: Didier Festal, Ecully; Denis Descours, Villeurbanne; Robert Bellemin, Lyon; Jacques Decerprit, Neyron, all of France

[73] Assignee: Lipha, Lyonnaise Industrielle Pharmaceutique, Lyon, France

[21] Appl. No.: 855,544

[22] Filed: Mar. 20, 1992

[30] Foreign Application Priority Data

Mar. 26, 1991 [FR] France .................. 91 03618

[51] Int. Cl.$^5$ .............. A61K 31/505; A61K 31/405; C07D 239/02; C07D 209/16
[52] U.S. Cl. ............................ 514/269; 514/339; 514/415; 544/319; 546/273; 548/504; 548/510
[58] Field of Search ............ 548/504, 510; 546/273; 544/319; 514/415, 269, 339

[56] References Cited

PUBLICATIONS

CA 115 (13): 135908r Preparation of . . . 5-lipoxygenase inhibitors. Brooks et al., p. 963, 1991.
CA 115(23): 256019K Preparation of . . . immunotherapeutic agents, Schultz et al., p. 848, 1991.
CA 115 (23): 256179n Preparation of . . . LTD$_4$ antagonists, Huang et al., p. 867, 1991,

*Primary Examiner*—Mary C. Lee
*Assistant Examiner*—Joseph K. McKane
*Attorney, Agent, or Firm*—Oblon, Spivak, McClelland, Maier & Neustadt

[57] ABSTRACT

The invention relates to indole derivatives of formula 1,

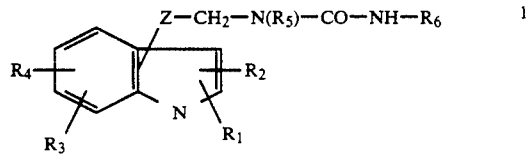

in which:

$R_1$ and $R_2$ represent H, alkyl, alkenyl, cycloalkyl, N-alkylamino- or N,N-dialkylaminoalkyl, benzyl, pyridylmethyl or phenyl, optionally substituted, $R_3$ and $R_4$ represent H, halogen, alkyl, alkoxy, alkylthio, $CF_3$, $NO_2$, N-alkylamino or N,N-dialkylamino, benzyl or phenyl, optionally substituted, $R_5$ represents H, alkyl, cycloalkyl or optionally substituted benzyl, $R_6$ denotes an alkyl, phenyl or heterocyclic radical, optionally substituted, Z denotes the bivalent radicals $-(CH_2)_n-C(R_7R_8)-(CH_2)_p-$, $-CH=CH-C(R_7R_8)-$ in which $n=0-2$, $p=0-2$ and $n+p \leq 2$, $R_7$ and $R_8$ represent H, alkyl, alkenyl, cycloalkyl, N-alkylamino, N,N-dialkylamino, N-alkylamino- or N,N-dialkylaminoalkyl, benzyl or phenyl, where appropriate substituted, or together form polymethylene or oxa-, thia- or azapolymethylene chains, as well as their tautomeric forms, to processes for preparing them and to their application as hypolipidaemic, antiatheromatous and antidiabetic pharmaceutical products.

8 Claims, No Drawings

INDOLE DERIVATIVES, PREPARATION PROCESSES AND MEDICINAL PRODUCTS CONTAINING THEM

The present invention relates to indole derivatives, to processes for preparing these compounds, to pharmaceutical compositions containing them and to their use as therapeutic products, in particular in the treatment of hyperlipidaemia and atherosclerosis.

Lipid deposits, in particular cholesterol deposits, in the vessels are known to be the source of the formation of atherome plaques, which are the cause of miscellaneous cardiovascular diseases; more precisely, atherome is a form of atherosclerosis characterised by an excessive accumulation of lipids, especially cholesterol esters, in the wall of the vessels; it was recently found that an enzyme, acylcoenzyme A:cholesterol acyltransferase (ACAT), was responsible for the esterification of cholesterol, and a correlation was demonstrated between an increase in the activity of this enzyme and the accumulation of cholesterol esters in the vessel wall; it is also known that dietary cholesterol is absorbed in free form, and is then esterified by intestinal ACAT and released into the blood circulation in the form of VLDL and/or chylomicrons.

Efforts have been made to develop products which inhibit ACAT and are capable of preventing the intestinal absorption of dietary and biliary cholesterol and of counteracting the deposition of cholesterol esters in the wall of the vessels.

This search for ACAT inhibitors led the inventors to prepare a new family of indole derivatives, and to find that these products unexpectedly manifest a potent inhibitory activity towards vascular ACAT combined with an intense antihyperlipidaemic effect on the various animal species.

These properties of the compounds of the invention make them especially useful, in particular for the treatment of hyperlipidaemia and atherosclerosis.

The invention relates more especially to the compounds of formula 1,

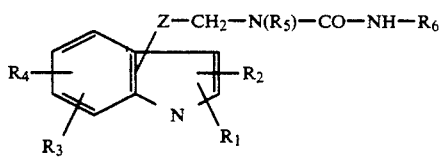

in which $R_1$ and $R_2$, which may be located at position 1-, 2- or 3- of the indole ring-system, independently represent a hydrogen atom, a linear alkyl radical having 1 to 12 carbon atoms or branched alkyl radical having 3 to 5 carbon atoms or alkenyl, cycloalkyl, N-alkylaminoalkyl or N,N-dialkylaminoalkyl radicals, or one of the substituents $R_1$ or $R_2$ represents a 2-pyridyl(or 3- or 4- pyridyl)methyl radical and the other a hydrogen atom, on the understanding that when the nitrogen atom of the indole ring-system is not substituted with any of the groups $R_1$, $R_2$ or $-Z-CH,-N(R_5)CONHR_6$, it is substituted with a hydrogen atom, $R_3$ and $R_4$, which may be located at position 4-, 5-, 6- or 7- of the indole ring-system, independently represent hydrogen or halogen atoms or alkyl, alkoxy or alkylthio radicals, or one of the substituents $R_3$ or $R_4$ denotes a hydrogen atom and the other substituent trifluoromethyl, nitro, N-alkylamino or N,N-dialkylamino radicals, or three of the substituents $R_1$, $R_2$, $R_3$ or $R_4$ have the meanings which have just been defined and the fourth represents a radical of formula 2

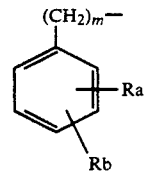

in which m can take the values 0, 1 or 2 and the substituents Ra and Rb independently denote hydrogen or halogen atoms or alkyl, alkoxy or alkylthio radicals, $R_5$ denotes a hydrogen atom, a linear alkyl radical having 1 to 12 carbon atoms or branched alkyl radical having 3 to 5 carbon atoms, a cycloalkyl radical or a radical of formula 2, in which m has the value 1 and Ra and Rb have the meanings defined above, $R_6$ denotes an alkyl radical or a radical of formula 3:

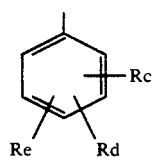

in which

Rc, Rd and Re independently denote hydrogen or halogen atoms or alkyl, alkoxy or alkylthio radicals, or two of the substituents Rc, Rd and Re can have the meanings which have just been defined and the third represents a trifluoromethyl radical, $R_6$ can also denote 5- or 6- membered heterocyclic radical containing one or two hetero atoms, and, where appropriate, substituted with one to three halogen atoms or alkyl or alkoxy radicals, Z, which can be attached to positions 1-, 2-, 3-, 4-, 5-, 6- or 7- of the indole ring-system, denotes the bivalent radicals of formula $-(CH_2)_n-C(R_7R_8)-(CH_2)_p-$ or $-CH=CH-C(R_7R_8)-$, in which n and p denote two integers which can take the values 0, 1 and 2, on condition that their sum (n+p) is not greater than 2, $R_7$ and $R_8$ in dependently represent a hydrogen atom, a linear alkyl radical having 1 to 12 carbon atoms or branched alkyl radical having 3 to 5 carbon atoms, alkenyl, cycloalkyl, N-alkylamino, N,N-dialkylamino, N-alkylaminoalkyl or N,N-dialkylaminoalkyl radicals or a group of formula 2 in which m can take the values 0 or 1 Ra and Rb have the meanings already defined, $R_7$ and $R_8$ together can also form a polynethylene chain $-(CH_2)_q-$, in which q can take the values 3 to 8 and which is capable, where appropriate, when q is not less than 5, of containing a double bond, $R_7$ and $R_8$ together can also form the chains: $-CH_2-O-(CH_2)_2-$, $-(CH_2)_2-O-(CH_2)_2-$, $-CH_2-S-(CH_2)_2-$, $-(CH_2)_2-S-(CH_2)_2-$, $-CH_2-N(R_9)-(CH_2)_2-$ or $-(CH_2)_2-N(R_9)-(CH_2)_2-$, $R_5$, $R_7$ and $R_8$ can also, when they represent cycloalkyl radicals, contain a double bond, $R_9$ represents an alkyl radical.

According to a preferred form of the invention, the subject of the latter is the compounds of formula 1 in which $R_1$ and $R_2$ represent hydrogen atoms or alkyl, N-alkylaminoalkyl or N,N-dialkylaminoalkyl radicals, $R_3$ and $R_4$ represent hydrogen or halogen atoms or alkyl or alkoxy radicals, $R_5$ represents a hydrogen atom, a linear alkyl radical or a group of formula 2 in which $m=1$ and $R_6$ denotes a radical of formula 3.

The term "alkyl" is understood to mean a hydrocarbon arrangement which, except where otherwise specified, is saturated, linear or branched, derived from the corresponding alkane by elimination of a hydrogen atom and comprises, more especially, 1 to 5 carbon atoms, such as, for example, methyl, ethyl, n-propyl, n-butyl, isopropyl, tert-butyl or 2,2-dimethylpropyl.

The term "alkenyl" characterises a linear or branched hydrocarbon radical comprising, more especially, 3 to 6 carbon atoms and containing a double bond, such as, for example, allyl, 3-butenyl or 2-methyl-2-propenyl.

The term "halogen" is understood, more specifically, to mean bromine, chlorine or fluorine.

"Alkoxy" or "alkylthio" is understood to mean an alkyl arrangement as defined above linked to the parent molecule via an oxygen or sulphur atom, such as, for example, methoxy, ethoxy, n-propoxy, isopropoxy, n-butoxy, tert-butyloxy, methylthio, ethylthio, n-propylthio or isopropylthio.

The terms "N-alkylamino" and "N,N-dialkylamino" denote, respectively, a nitrogen atom substituted with a hydrogen atom and an alkyl radical and substituted with two alkyl radicals, respectively, and the free valency of which forms the bond with the parent molecule.

The term "N-alkylaminoalkyl" or "N,N-dialkylaminoalkyl" is understood to mean an alkyl radical as defined above and substituted at the omega-position with an N-alkylamino or N,N-dialkylamino radical, respectively.

The term "cycloalkyl" characterises a saturated cyclic hydrocarbon arrangement derived from a cyclane such as cyclopropane, cyclopentane, cyclohexane, cycloheptane or cyclooctane, by elimination of a hydrogen atom.

"5- or 6-membered heterocyclic radical containing 1 or 2 hetero atoms" is understood to mean a radical derived, by elimination of a hydrogen atom, from a 5- or 6-membered ring and containing one or two hetero elements chosen from oxygen, sulphur or nitrogen, such as, for example, thiophene, furan, pyrrol, pyridine, thiazole, isothiazole, oxazole, isoxazole, imidazole, pyrimidine or pyrazine rings, in particular 2- or 3-thienyl or -furyl, 1-pyrrolyl, 2-, 4- or 5-oxazolyl, -thiazolyl or -imidazolyl, 3-, 4- or 5-isoxazolyl or -isothiazolyl, 2-, 3- or 4-pyridyl, 2-pyrimidinyl or 2- or 3-pyrazinyl radicals; "optionally fused with a benzene ring" is understood to mean radicals derived, by elimination of a hydrogen atom, from the bicyclic systems resulting from fusion of the abovementioned heterocycles with benzene, such as the benzothiophene, benzofuran, indole, benzimidazole, quinoline, isoquinoline, quinoxaline or quinazoline ring-systems, especially benzo[b]thien-5-yl or -6-yl or benzo[b]furan-5-yl or -6-yl, 2-, 3-, 5- or 6-indolyl, 2-, 5- or 6-benzimidazolyl, 2-, 3-, 4-, 5-, 6- or 7-quinolyl, 1-, 3-, 4-, 6- or 7-isoquinolyl, 2-, 3-, 6- or 7- quinoxalinyl or 2-, 4-, 6- or 7-quinazolinyl radicals.

The compounds of formula 1 can contain one or more centres of asymmetry, in particular when the substituents $R_7$ and $R_8$ are different, generating diastereoisomers, enantiomers and racemates which also form part of the invention.

It falls within the normal competence of the expert to isolate or synthesise an optically active form of a compound of formula 1, for example by resolution of a racemate or by synthesis starting from an optically active compound, and to determine the biological properties of the isomers thereby isolated according to the experiments described below.

The mixtures of stereoisomers may be separated by the standard methods at whichever of the stages is most suitable; standard methods is understood to mean the collective processes familiar to the expert, such as, for example, crystallisation, chromatography or the formation of combinations with optically active compounds.

The compounds of formula 1 can exist in one or more tautomeric forms which also form part of the invention.

As specific compounds of the invention, the compounds which follow, the structural formulae of which appear at the end of the description, may be mentioned solely by way of example.

Compound No. 1: $N^1$-(2,6-Diisopropylphenyl)-$N^2$-[1-(methyl-3-indolyl)cyclopentylmethyl]urea.

Compound No. 2: $N^1$-[1-(1-Indolyl)cyclopentylmethyl]-$N^2$-(2,6-diisopropylphenyl)urea Compound No. 3: $N^1$-(2,6-Diisopropylphenyl)-$N^2$-{3-[1-(1-methyl-3-indolyl)cyclopentyl]propyl}urea.

Compound No. 4: $N^1$-(2,6-Diisopropylphenyl)-$N^2$-{2-[1-(1-methyl-3-indolyl)cyclopentyl]ethyl}urea.

Compound No. 5: $N^1$-Benzyl-$N^2$-(2,6-diisopropylphenyl)-$N^1$-[1-(1-methyl-3-indolyl cyclopentylmethyl]urea.

Compound No. 6: $N^1$-[1-(1-Methyl-3-indolyl)cyclopentyl-methyl]-$N^2$-phenylurea.

Compound No. 7: $N^1$-[2-(3-Indolyl)ethyl]-$N^2$-(2,6-diisopropylphenyl)urea.

Compound No. 8: $N^1$-(2,4-Difluorophenyl)-$N^2$-[1-(1-methyl-3-indolyl)cyclopentylmethyl]urea.

Compound No. 9: $N^1$-(2,6-Diisopropylphenyl)-$N^2$-[3-methyl-2-(1-methyl-3-indolyl)butyl]urea.

Compound No. 10: $N^1$-tert-Butyl-$N^2$-[1-(1-methyl-3-indolyl)cyclopantylmethyl]urea.

Compound No. 11: $N^1$-(2,6-Diisopropylphenyl)-$N^2$-[2-(1-methyl-3-indolyl)propyl]urea.

Compound No. 12: $N^1$-[1-(1-Benzyl-3-indolyl)cyclopentylmethyl]-$N^2$-(2,6-diisopropylphenyl)urea.

Compound No. 13: $N^1$-[1-(1-Ethyl-3-indolyl)cyclopentylmethyl]-$N^2$-(2,6-diisopropylphenyl)urea.

Compound No. 14: $N^1$-(2,6-Diisopropylphenyl)-$N^2$-[2-(1-methyl-3-indolyl)butyl]urea.

Compound No. 15: $N^1$-(2,6-Diisopropylphenyl)-$N^2$-[1-(1,5-dimethyl-3-indolyl)cyclopentylmethyl]urea.

Compound No. 16: $N^1$-(2,6-Diisopropylphenyl)-$N^2$-[1-(1-methyl-3-indolyl)cyclohexylmethyl]urea.

Compound No. 17: $N^1$-[2-Ethyl-2-(1-methyl-3-indolyl)-2-butyl]-$N^2$-(2,6-diisopropylphenyl)urea.

Compound No. 18: $N^1$-(2,6-Diisopropylphenyl)-$N^2$-[2-methyl-2-(1-methyl-3-indolyl)propyl]urea.

Compound No. 19: $N^1$-[1-(1-Isopropyl-3-indolyl)cyclopentylmethyl]-$N^2$-(2,6-diisopropylphenyl)urea.

Compound No. 20: $N^1$-[1-(1-Allyl-3-indolyl)cyclopentylmethyl]-$N^2$-(2,6-diisopropylphenyl)urea.

Compound No. 21: $N^2$-(2,6-Diisopropylphenyl)-$N^2$-[2-(1-methyl-3-indolyl)-2-phenylethyl]urea.

Compound No. 22: $N^1$-[2-Allyl-2-(1-methyl-3-indolyl)-4-pentenyl]-$N^2$-(2,6-diisopropylphenyl)urea.

Compound No. 23: $N^1$-(2,6-Diisopropylphenyl)-$N^2$-[1-(1-phenyl-3-indolyl)cyclopentylmethyl]urea.

Compound No. 24: $N^1$-(2,6-Diisopropylphenyl)-$N^2$-[1-(1-methyl-3-indolyl)cyclobutylmethyl]urea.

Compound No. 25: $N^1$-[2-Butyl-2-(1-methyl-3-indolyl)-(1 hexyl]-$N^2$-(2,6-diisopropylphenyl)urea.

Compound No. 26: $N^1$-(2,6-Diisopropylphenyl)-$N^2$-[2-(1-methyl- 3-indolyl)-4-pentenyl]urea.

Compound No. 27: $N^1$-[1-(1-Heptyl-3-indolyl)cyclopentylmethyl]-$N^2$-(2,6-diisopropylphenyl)urea.

Compound No. 28: $N^1$-[1-(1-Butyl-3-indolyl)cyclopentylmethyl]-$N^2$-(2,6-diisopropylphenyl)urea.

Compound No. 29: $N^1$-(2,6-Diisopropylphenyl)-$N^2$-[2-(1-methyl-3-indolyl)hexyl]urea.

Compound No. 30: $N^1$-(2,6-Diisopropylphenyl)-$N^2$-[2-(1-methyl-3-indolyl)nonyl]urea.

Compound No. 31: $N^1$-(2,6-Diisopropylphenyl)-$N^2$-[4,4-dimethyl-2-(1-methyl-3-indolyl)pentyl]urea.

Compound No. 32: $N^1$-(2,6-Diisopropylphenyl)-$N^2$-[2-(1-methyl-3-indolyl)-3-phenylpropyl]urea.

Compound No. 33: $N^1$-(2,6-Dichlorophenyl)-$N^2$-[1-(1-methyl-3-indolyl)cyclopentylmethyl]urea.

Compound No. 34: $N^1$-(2,6-Diisopropylphenyl)-$N^2$-[1-(1-methyl-3-indolyl)cycloheptylmethyl]urea.

Compound No. 35: $N^1$-(2,6-Diisopropylphenyl)-$N^2$-[1-(1-methyl-3-indolyl)tetrahydro-4-pyranylmethyl]urea.

Compound No. 36: $N^1$-(2,6-Diethylphenyl)-$N^2$-[1-(1-methyl-3-indolyl)cyclopentylmethyl]urea.

Compound No. 37: $N^1$-(2,6-Diisopropylphenyl)-$N^2$-(1-[1-(2-dimethylaminoethyl)-3-indolyl]cyclopentylmethyl}urea.

Compound No. 38: $N^1$-{1-[1-(4-Fluorobenzyl)-3-indolyl]-cyclopentylmethyl}-$N^2$-(2,6-diisopropylphenyl)urea.

Compound No. 39: $N^1$-(2,4,6-Trimethoxyphenyl)-$N^2$-[1-(1-methyl-3-indolyl)cyclopentylmethyl]urea.

Compound No. 40: $N^1$-(4,6-Dimethoxy-5-pyrimidinyl)-$N^2$-1-(1-methyl-3-indolyl)cyclopentylmethyl]urea.

Compound No. 41: $N^1$-(2,6-Diisopropylphenyl)-$N^2$-[1-(5-methoxy-1-methyl-3-indolyl)cyclopentylmethyl]urea.

Compound No. 42: $N^1$-(2,6-Diisopropylphenyl)-$N^2$-[4-dimethylamino-2-(1-methyl-3-indolyl)butyl]urea.

Compound No. 43: $N^1$-(2,6-Diisopropylphenyl)-$N^2$-[5-methyl-2-(1-methyl-3-indolyl)-4-hexenyl]urea.

Compound No. 44: $N^1$-(2,6-Diisopropoxyphenyl)-$N^2$-[1-(1-methyl-3-indolyl)cyclopentylmethyl]urea.

Compound No. 45: $N^1$-(2,6-Diisopropylphenyl)-$N^2$-{1-[1-(3-pyridylmethyl)-3-indolyl]cyclopentylmethyl}urea.

Compound No. 46: $N^1$-Benzyl-$N^1$-[1-(1-methyl-3-indolyl)-cyclopentylmethyl]-$N^2$-(2,6-dimethylphenyl)urea.

Compound No. 47: $N^1$-Benzyl-$N^2$-(2,6-dichlorophenyl)-$N^1$-[1-(1-methyl-3-indolyl)cyclopentylmethyl]urea.

Compound No. 48: $N^1$-Benzyl-$N^2$-(2,4-difluorophenyl)-$N^1$-[1-(1-methyl-3-indolyl)cyclopentylmethyl]urea.

Compound No. 49: $N^2$-(2,6-Diisopropylphenyl)-$N^1$-methyl-$N^1$-[1-(1-methyl-3-indolyl)cyclopentylmethyl]urea.

Compound No. 50: $N^1$-(2,6-Diisopropylphenyl)-$N^2$-[1-(1,2-dimethyl-3-indolyl)cyclopentylmethyl]urea.

Compound No. 51: $N^1$-(2,6-Diisopropylphenyl)-$N^2$-1-(1-methyl-2-phenyl-3-indolyl)cyclopentylmethyl]urea.

Compound No. 52: $N^1$-(2,6-Diisopropylphenyl)-$N^2$-[1-(1,3-dimethyl-2-indolyl)cyclopentylmethyl]urea.

Compound No. 53: $(-)$-$N^1$-(2,6-Diisopropylphenyl)-$N^2$-[2-(1-methyl-3-indolyl)hexyl]urea.

Compound No. 54: $(+)$-$N^1$-(2,6-Diisopropylphenyl)-$N^2$-[2-(1-methyl-3-indolyl)hexyl]urea.

The invention also relates to processes for preparing the compounds of the formula 1, characterised in that they entail at least, as illustrated in Scheme 1 below, a) the reduction of a nitrile of general formula 6, in which Z, $R_1$, $R_2$, $R_3$ and $R_4$ have the general or particular meanings already defined and Z can also represent a radical $—C(R_7R_8)—CH=CH—$, b) the reaction of an amine of general formula 5, in which Z, $R_1$, $R_2$, $R_3$ and $R_4$ have the general or particular meanings already defined, with a halogenated compound of formula $R_5$-X in which X denotes a bromine, chlorine or iodine atom and $R_5$ has the general or particular meanings already stated, or alternatively with an aldehyde of formula $R_{10}$-CHO or an acid chloride or anhydride of formula $R_{10}$-COCl or $(R_{10}$-CO$)_2$O, respectively, in which formulae $R_{10}$ represents an alkyl radical optionally containing a double bond or a radical of formula 2 defined above in which m is equal to 0 and Ra and Rb have the general or particular meanings already defined, followed by reduction of the corresponding imine or amide thereby obtained, c) the reaction of phosgene and a suitable amine of formula $R_6NH_2$, or of an icocyanate of formula $R_6NCO$, or alternatively of a trichloroacetamide of general formula $Cl_3C—CO—NHR_6$, in which formulae $R_6$ has the general or particular meanings defined above, with an amine of general formula 4 in which Z, $R_1$, $R_2$, $R_3$, $R_4$ and $R_5$ have the general and particular meanings already defined.

Scheme 1

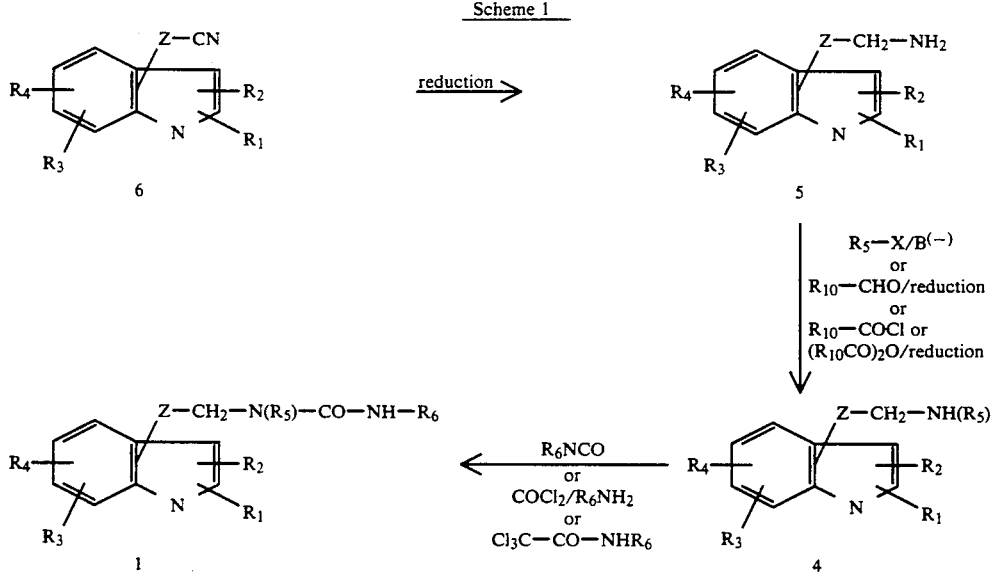

The reduction according to a) consists of a catalytic hydrogenation or alternatively of a chemical reduction, in particular in the case where the intermediate compound 6 to be reduced contains one or more hydrogenation-sensitive groups which it is not desired to reduce; the catalytic hydrogenation is performed at atmospheric pressure or under a pressure which can range up to 180 bars, in the presence of a metal catalyst such as, for example, palladium dispersed on charcoal or Raney nickel, and a base which is generally sodium hydroxide in pellet form, ammonia or alternatively a tertiary aliphatic amine such as triethylamine, in a solvent, preferably polar, which is compatible with hydrogen, such as, for example, tetrahydrofuran or an alcohol such as methanol, ethanol or isopropanol; the chemical reduction is carried out preferably using lithium aluminium hydride as a reducing agent, although other agents for reducing the nitrile function can also be suitable, in a solvent commonly used with this reducing agent, such as tetrahydrofuran or diethyl ether, at a temperature between room temperature and the refluxing temperature of the solvent used, but preferably at the refluxing temperature of the solvent used.

The alkylation according to b) is carried out in the presence of a basic agent, preferably a tertiary amine such as, for example, triethylamine, in a suitable solvent, preferably a polar solvent such as, for example, tetrahydrofuran, and generally at the refluxing temperature of the solvent used; the condensation according to b) of an aldehyde with an amine 5, as an alternative to the alkylation, is performed in a solvent or solvent mixture which is inert with respect to the reactants and immiscible with water; in particular, aromatic hydrocarbons, especially alkylbenzenes such as toluene or xylene, may be used as solvents; it is possible, where appropriate, in order to facilitate the formation of the imine, to add a dehydrating agent such as, for example, para-toluenesulphonic acid; it is preferable to work at the refluxing temperature of the solvent used; the imine thereby obtained is reduced directly to the amine 4 with sodium borohydride; this reduction is performed in a suitable solvent such as tetrahydrofuran or an alcohol which can be, for example, methanol or alternatively ethanol, and at a temperature between room temperature and the refluxing temperature of the solvent used; the acylation according to b), as another process for synthesis of the compounds 4, is carried out in the presence of a basic agent, preferably a tertiary aliphatic amine such as, for example, triethylamine, in a solvent which is preferably tetrahydrofuran or alternatively an aromatic hydrocarbon such as, for example, benzene or an alkylbenzene such as toluene or xylene, or alternatively a halogenated solvent such as chloroform or methylene chloride, and preferably at the boiling point of the solvent used; the amide thereby obtained is then reduced with lithium aluminium hydride in diethyl ether or tetrahydrofuran at the boiling point of the solvent used.

Condensation of an isocyanate according to c) is preferably performed in an alkane such as pentane or hexane, or alternatively an ether such as diisopropyl ether or diethyl ether, or alternatively, in the case of a less soluble amine, in ethyl acetate and at the temperature best suited for obtaining the reaction, which is generally room temperature; the reaction with phosgene according to c), as an alternative method for preparing compounds of the invention, is carried out in an aromatic hydrocarbon such as, for example, toluene, in the presence of a basic agent such as triethylamine and at a temperature close to room temperature; when the formation of the intermediate carbamoyl chloride is complete, it is reacted with the desired amine at a temperature between room temperature and the boiling point of the solvent used; the aminocarbonylation according to c), in which a trichloroacetamide of general formula $Cl_3C-CO-NH-R_6$ is used, is performed by heating in an aprotic polar solvent such as, for example, N,N-dimethyl-formamide, tetramethylurea, N-methylpyrrolidone or alternatively hexamethylphosphorotriamide, in the presence of a basic agent which is preferably an alkali metal carbonate or alkaline earth metal carbonate such as sodium or potassium carbonate, and at a temperature between room temperature and 110° C. and preferably at a temperature in the region of 110° C.

The invention also relates to those intermediate compounds corresponding to the general formulae 4, 5 and 6 which are new, as well as to processes for their synthesis.

The intermediate nitriles of general formula 6 in which Z represents a bivalent radical of general formula —(CH$_2$)$_n$—C(R$_7$R$_8$)—(CH$_2$)$_p$— in which n=p=0 and R$_7$ and R$_8$ have the general or particular meanings already specified may be prepared according to Scheme 2 below, according to which a suitable N,N-dimethylaminomethylindole of general formula 7, in which R$_1$, R$_2$, R$_3$, and R$_4$ have the general or particular meanings already stated, is alkylated with methyl iodide or dimethyl sulphate, in a solvent, preferably polar, such as acetonitrile, acetone or alternatively ethyl acetate, and preferably at the refluxing temperature of the solvent used, and the indolylmethyltrimethylammonium iodide thereby obtained is then treated with sodium cyanide or potassium cyanide, in a polar solvent or mixture of polar solvents such as, for example, ethanol or N,N-dimethylformamide or ethanol/water or N,N-dimethylformamide/water mixtures, or alternatively an N-alkylation of an indole compound of general formula 8, in which R$_1$, R$_2$, R$_3$ and R$_4$ have the general or particular meanings already defined, is carried out with chloroacetonitrile in the presence of a basic agent such as sodium hydride or an alkali metal alcoholate such as, for example, potassium tert-butylate in a polar solvent such as N,N-dimethylformamide or dimethyl sulphoxide, or alternatively in the presence of sodium hydroxide and a phase transfer catalyst; the nitrile thereby obtained can, where appropriate, be mono- or dialkylated with halides of formula R$_7$—X or R$_8$—X or dihalides of formula X—(CH$_2$)$_q$—X, in which formulae q, R$_7$ and R$_8$ have the general or particular meanings specified above and, where appropriate, R$_7$ and R$_8$ contain a double bond, in the presence of a basic agent such as sodium hydride or alternatively an alkali metal amide or alkaline earth metal amide such as sodium amide or lithium diisopropyl amide, in a suitable solvent or mixture of suitable solvents such as benzene or toluene or alternatively diethyl ether, and preferably at a temperature generally of between 20° and 80° C., or between −50° C. and room temperature in the special case where lithium diisopropylamide is the agent employed.

The N,N-dimethylaninomethylindoles of general formula 7 defined above are prepared according to the following Scheme 3

Scheme 3

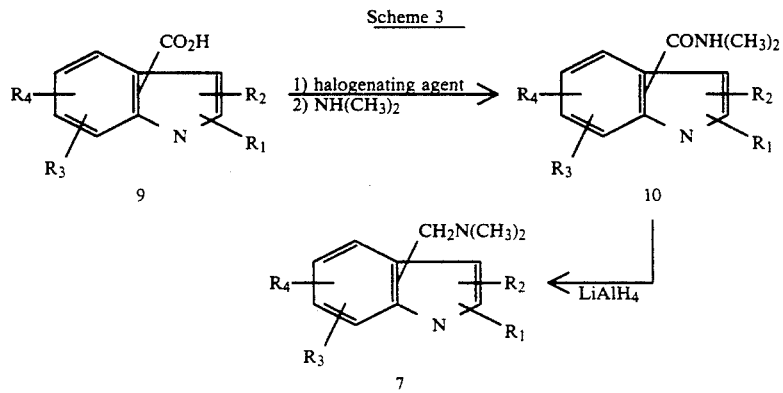

according to which an acid of general formula 9, in which R$_1$, R$_2$, R$_3$ and R$_4$ have the general or particular meanings already defined, is converted to the N,N-dimethylcarboxamides of general formula 10, by treating it successively with a halogenating agent such as, for example, phosphorus trichloride or pentachloride or alternatively thionyl chloride in a inert solvent such as, for example, an aromatic hydrocarbon such as benzene or toluene or alternatively a halogenated solvent such as methylene chloride or chloroform, and at the most suitable temperature for the reaction to proceed, which is generally the refluxing temperature of the solvent used, and then with N,N-dimethylamine; the N,N-dimethylindolecarboxamides of general formula 10 thereby formed are then reduced with an agent for reducing the

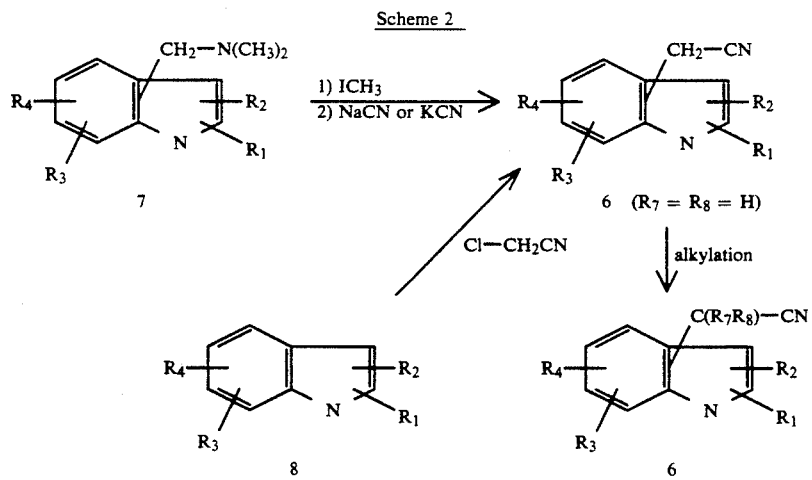

carboxamide function, preferably lithium aluminium hydride, in a suitable solvent such as, for example, diethyl ether or tetrahydrofuran and at the refluxing temperature of the solvent used.

The N,N-dimethylaminomethylindoles of general formula 7 in which the N,N-dimethylaminomethyl radical is at position 3- of the indole ring may also be prepared by treating the corresponding nor-indoles under the Mannich conditions described by H. KUHN and O. STEIN, Chem. Ber., 1937, 70, 567 and by E. WALTON et al., J. Med. Chem., 1965, 8, 204.

The intermediate nitriles of general formula 6 in which Z represents a bivalent radical of formula —CH=CH—C($R_7R_8$)— in which $R_7$ and $R_8$ have the general or particular meanings defined above may be prepared according to Scheme 4 below, according to which a formylpropenylindole of general formula 11, in which $R_1$, $R_2$, $R_3$ and $R_4$ have the general or particular meanings already specified, is reacted with a diethyl phosphorocyanidate in the presence of lithium cyanide or lithium diisopropylamide in tetrahydrofuran to give the cyanophosphate 12, which is then treated with samarium iodide to give the nitrile 13; the reaction is performed at a temperature which can be between room temperature and the refluxing temperature of the solvent used. The nitrile 13

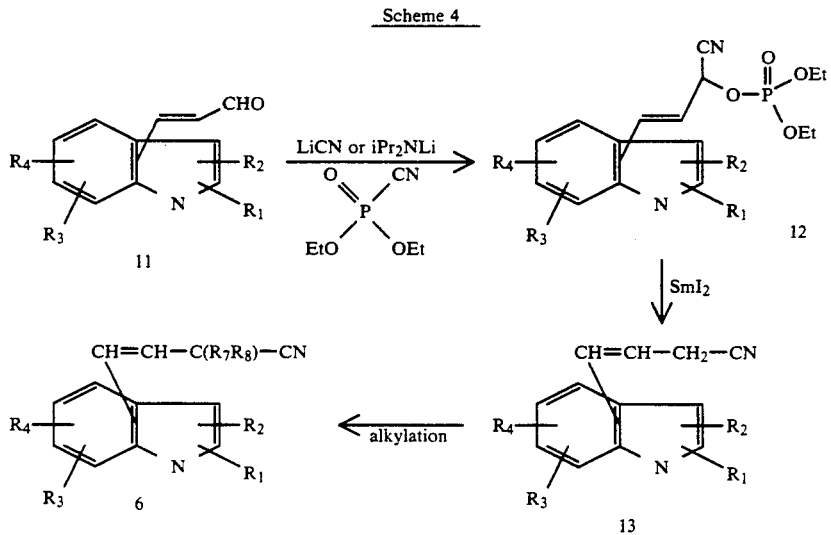

is then alkylated under the conditions described above to give the nitrile 6.

The aldehydes of general formula 11 may be prepared by a Vilsmeier reaction on the corresponding nor-indole using dimethylaminoacrolein under the conditions described by G. F. SMITH, J. Chem. Soc., 1954, 3842.

The intermediate nitriles of general formula 6 in which Z denotes a bivalent radical of formula —($CH_2$)$_n$—C($R_7R_8$)—($CH_2$)$_p$— in which $R_7$ and $R_8$ have the general or particular meanings already specified and $n=0$ and $p=1$ are prepared according to the following Scheme 5

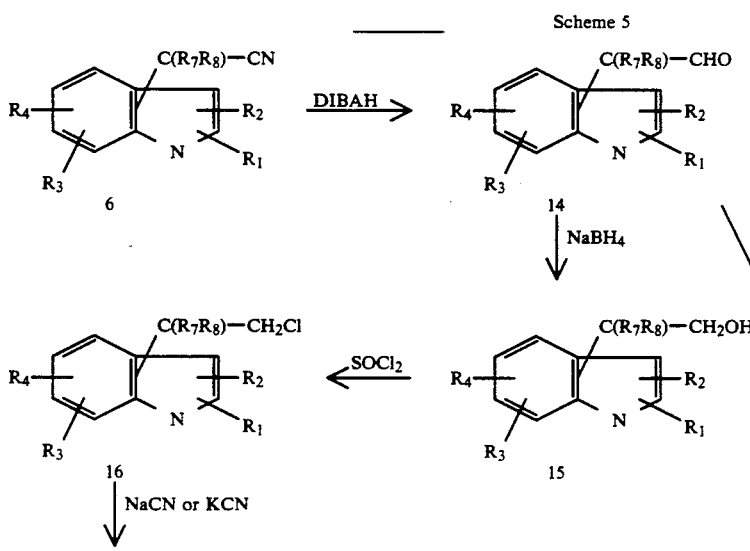

-continued
Scheme 5

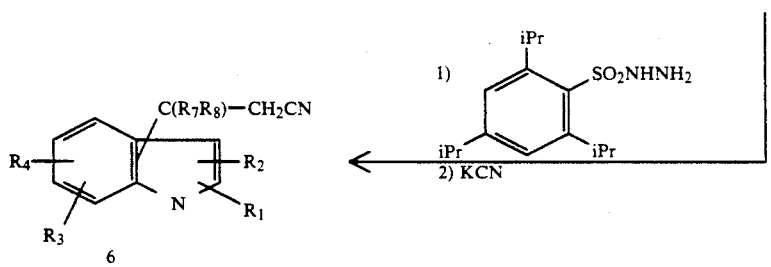

according to which a nitrile of general formula 6 in which $Z=-(CH_2)_n-C(R_7R_8)-(CH_2)_p-$, $n=p=0$ and $R_7$ and $R_8$ have the general or particular meanings already defined is reduced with diisobutylaluminium hydride to the corresponding aldehyde of general formula 14, using diethyl ether or tetrahydrofuran or alternatively methylene chloride or alternatively toluene as a solvent, at a temperature lying between room temperature and the boiling point of the solvent used, which aldehyde is then reduced to the indoleethanol of general formula 15 with sodium borohydride in a polar solvent such as tetrahydrofuran or an alcohol such as methanol, ethanol or isopropanol and at a temperature which is preferably the boiling point of the solvent employed; the indoleethanol of general formula 15 thereby prepared is then halogenated with thionyl chloride or any other similar halogenating agent, in benzene or in a chlorinated solvent such as chloroform or methylene chloride and at the refluxing temperature of the solvent used; the chloro derivative of general formula 16 thereby obtained is then treated with sodium cyanide or potassium cyanide in a polar solvent or mixture of polar solvents such as ethanol, tetrahydrofuran or N,N-dimethylformamide or an ethanol water or N,N-dimethylformamide/water mixture and at a temperature between room temperature and 80° C., generally closer to 80° C. than to room temperature.

An alternative, according to Scheme 5, for preparing the nitriles of general formula 6 in which $Z=-(CH_2)_n-C(R_7R_8)-(CH_2)_p-$, $n=0$, $p=1$ and $R_7$ and $R_8$ have the general or particular meanings already defined consists in reacting at room temperature an aldehyde of general formula 14 with 2,4,6-triisopropylbenzenesulphonohydrazide in a polar solvent such as, for example, tetrahydrofuran, and then treating the corresponding sulphonylhydrazone thereby obtained with potassium cyanide, preferably in an alcohol such as methanol, for example, and at the refluxing temperature of the solvent used.

The intermediate nitriles of general formula 6 in which Z represents a bivalent radical of formula $-(CH_2)_n-C(R_7R_8)-(CH_2)_p-$ in which $R_7$ and $R_8$ have the general and particular meanings already defined and $n=1$ and $p=0$ are prepared according to the following Scheme 6

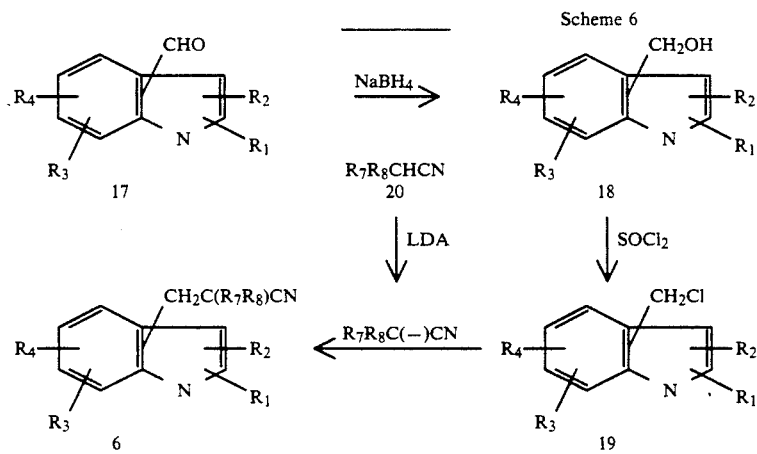

Scheme 6 according to which an aldehyde of general formula 17 is converted to a halide of general formula 19, in which $R_1$, $R_2$, $R_3$ and $R_4$ have the general or particular meanings defined above, using the same reaction sequence as that in Scheme 5 above and according to the same working conditions; the chloride of general formula 19 is then treated with a suitable acetonitrile of general formula 20 which has been converted beforehand to the lithium derivative with a strong base which is preferably lithium diisopropylamide; these two reactions are carried out in a suitable solvent such as diethyl ether or tetrahydrofuran, at low temperature, normally in the region of $-70°$ C. up to room temperature in the case of the metalation of the nitrile 20, and generally at the refluxing temperature of the solvent used in the case of the condensation of the lithium derivative with the chloro derivative 19.

The aldehydes of general formula 17 are prepared according to the following Scheme 7

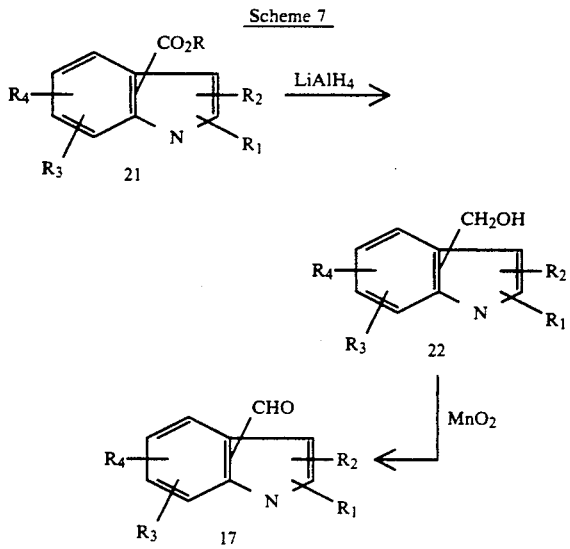

Scheme 7 according to which an alkyl indolecarboxylate of general formula 21, in which $R_1$, $R_2$, $R_3$ and $R_4$ have the general or particular meanings specified above and R denotes an alkyl radical, preferably a methyl or ethyl radical, is reduced; this reduction is carried out with an agent for reducing the ester function, such as, for example, lithium aluminium hydride, in the appropriate solvent which can be, for example, ether or tetrahydrofuran and at the reflux temperature of the solvent used ; the indolemethanol thereby obtained is then oxidised with manganese dioxide under the conditions described by J. HARLEY-MASON and E. H. PAVRI, J. Chem. Soc., 1963, 2565 and by H. PLIENINGER, M. HOBEL and V. LIEDE, Chem. Ber., 1963, 96, 1618.

The aldehydes of general formula 17 in which the formyl radical is at position 3- of the indole ringsystem may also be prepared by a Vilsmeier reaction on the corresponding nor-indole under the conditions described by G. F. SMITH, J. Chem. Soc., 1954, 3842.

The intermediate nitriles of general formula 6 in which Z represents a bivalent radical of formula —$C(R_7R_8)$—CH=CH— in which $R_7$ and $R_8$ can have the general or particular meanings already stated, are prepared according to the following Scheme 8

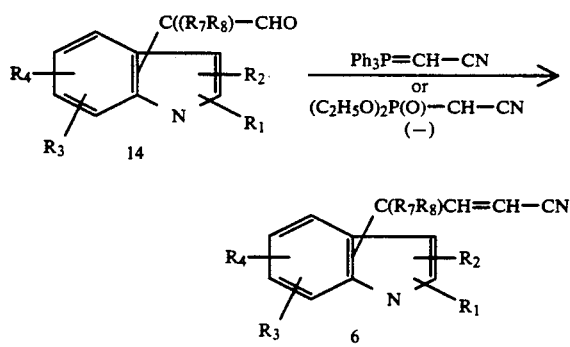

according to which cyanomethylenetriphenylphosphorane or the corresponding phosphonate is reacted with an indoleacetaldehyde of general formula 14 defined above, in a solvent such as, for example, acetonitrile or an aromatic hydrocarbon such as benzene or toluene and at a temperature which can be between room temperature and the reflux temperature of the solvent used.

The compounds of formula 1 have the property of inhibiting acylcoenzyme A:cholesterol acyltransferase (ACAT), and consequently exert a hypolipidaemic and antiatheromatous action; some of the compounds of formula 1 also manifest hypoglycaemic properties.

These properties of the compounds of the invention make it especially advantageous to use them as a medicinal product for the treatment or prevention of hypolipidaemia, atherosclerosis and diabetes, more particularly because these pathologies are often associated with one another.

The pharmacological properties of the compounds of the invention were demonstrated by the following tests:

Test A: measurement of the inhibition of aortic ACAT in vitro in rabbits: male New Zealand rabbits weighing between 2.2 and 2.5 kg, subjected beforehand for 15 days to a diet enriched with 1.25% of cholesterol, are sacrificed by cervical dislocation; the aorta is removed, dissected and homogenised in order to prepare the microsomal fraction of it by ultracentrifugation; these microsomes are incubated in the presence of [$^{14}$C]oleylcoenzyme A in accordance with the method described by P. J. GILLIES et al., Exp. and Mol. Pathol., 1986, 44, 329–339; the lipids are extracted from the incubate with a methanol/chloroform mixture and the [$^{14}$C]oleylcholesterol is separated by TLC: the latter compound represents a measure of the ACAT activity, and the results were expressed in the form of a 50% inhibitory concentration ($IC_{50}$), representing the concentration of compound which inhibits the ACAT activity by 50%.

Test B: measurement of the hypocholesterolaemic effect in rodents: male Wistar rats weighing 200–220 g are subjected to a diet enriched with 2.5% of cholesterol for 8 days; on the last two days, they are treated orally with the test product 24 hours and 4 hours before being sacrificed by exsanguination: the blood cholesterol level is evaluated on an aliquot fraction of serum by an automated enzymatic method. The results are expressed in the form of a 25% effective dose ($ED_{25}$) in mg per kg of body weight, representing the quantity of compound which lowers the blood cholesterol level by 25%.

Test C: measurement of the inhibition of intestinal absorption in rats; male Wistar rats weighing 230–250 g, fasted for 24 hours, are treated simultaneously with the test product administered orally and with Triton WR-1339 administered I.V.; one hour later, they are again treated orally with [$^{3}$H]cholesterol; three hours later, under ether anaesthesia, 1 ml of blood is withdrawn from the animals' retro-orbital sinus: the blood radioactivity, evaluated on 0.1 ml of serum, represents a measure of the absorption of the [$^{3}$H]cholesterol administered. The results are expressed in the form of a 50% effective dose ($ED_{50}$) in mg per kg of body weight, representing the quantity of compound which inhibits the intestinal absorption of cholesterol by 50%.

Test D: measurement of the hypoglycaemic effect: male Swiss mice weighing 26–28 g are treated orally with the test product. One hour later, the animals are sacrificed by exsanguination, and the blood sugar level is measured on an aliquot fraction of plasma by an enzymatic method employing glucose oxidase.

For the compound No. 1, for example, an $IC_{50}$ of $46 \times 10^{-9}$ mol.l$^{-1}$ was obtained in test A, an $ED_{25}$ of 0.098 mg.kg$^{-1}$ in test B, an $ED_{50}$ of 0.176 mg.kg$^{-1}$ in test C and a significant lowering of the blood sugar level of 21% at a dose of 60 mg.kg in test D.

The animal toxicities of the compounds of the invention were also evaluated, in particular in rats and mice, and it was shown that the compounds of the invention are especially well tolerated since, at orally administered doses of more than 3,200 mg.kg$^{-1}$, no mortality was observed.

These properties of the compounds of the invention make it especially advantageous to use them as pharmaceutical products, in particular for the treatment of hypolipidameia, atherosclerosis and diabetes.

The pharmaceuticalproducts of the invention are characterised in that they contain an effective quantity of at least one compound of general formula 1 in combination with a pharmacologically acceptable vehicle and, where appropriate, with any other product which is acceptable from a pharmaceutical standpoint, which can be inert or physiologically active.

These pharmaceutical products may be administered according to a wide variety of different forms of administration, for example in solid forms such as tablets, capsules including hard gelatin capsules, granules, powders, suppositories, and the like, or liquid forms such as syrups, elixirs or injectable solutions; in these compositions, the active principle can be, for example, mixed with one or more inert diluents such as lactose or starch and these compounds can additionally comprise substances other than diluents, for example lubricants such as talc or magnesium stearate; when elixirs, syrups or aqueous suspensions for oral administration are desired, the essential active ingredient can be combined therein with various sweeteners and/or flavourings, where appropriate emulsifiers and/or suspending agents, as well as diluents such as water, ethanol, propylene glycol, and various similar combinations.

These pharmaceutical compositions according to the invention generally take the form of single-dose preparations which can contain a quantity of active principle of between 10 and 100% of their total weight, and preferably lying within the range 10 to 60%.

When the compound of the invention is used as a hypolipidaemic or antiatherosclerotic agent or in the treatment of diabetes, the dosage adopted and the number of administrations are dependent on the patient's sex and weight and the acuteness of his or her symptoms, as well on the nature and degree of the expected therapeutic effect. In general, orally, it is preferably administered at doses of 10 to 500 mg per day in one or more portions, corresponding for an adult of average weight 70 kg to a dose range of approximately 0.15 to 7 mg per kilo per day.

The example which follows, given without implied limitation, illustrates a composition of this type.

EXAMPLE

| Active principle: compound No. 1 | 50 mg |
| --- | --- |
| Lactose | 69 mg |
| Dicalcium phosphate | 69 mg |
| Sodium carboxymethylcellulose | 10 mg |
| Magnesium stearate | 2 mg |

The invention is illustrated by the non-limiting examples described below, in which:

all the evaporations are performed, except where otherwise stated, in a rotary evaporator under reduced pressure, the temperatures are expressed in degrees centigrade (°C.), when "room temperature" is stated, this means a temperature which can be between 18° and 25° C., except where otherwise stated, the degree of progress of the reaction is monitored by thin-layer chromatography (TLC), the new compounds are, where appropriate, characterised by their physical constants: melting point designated m.p., or boiling point designated b.p. followed, where appropriate, by a statement of the pressure expressed in millibars, the nuclear magnetic resonance spectra are, except where otherwise stated, proton resonance spectra and are recorded at 60 MHz in the presence of tetramethylsilane as an internal standard; the chemical shifts are stated in ppm; the signals are described by the following abbreviations: s singlet, d=doublet, ps=pseudo-singlet, dd=doublet of doublet, t=triplet, q=quartet, hept.-=heptuplet, M=multiplet, the infrared spectra of the compounds are recorded using samples dispersed in potassium bromide in the case of solid compounds, or alternatively as a film in the case of liquids.

EXAMPLE 1

$N^1$-(2,6-Diisopropylphenyl)-$N^2$-[1-(1-methyl-3-indolyl)-cyclopentylmethyl]urea (compound No. 1, formula 1: $R^1$=1-$CH_3$, $R_2$=$R_3$=$R_4$=$R_5$=H, $R_6$=2,6-diisopropylphenyl, Z=-$(CH_2)_n$-$C(R_7R_8)$-$(CH_2)_p$- at position 3-, n=p=0, $R_7$-$R_8$=-$(CH_2)_4$-).

Stage 1

1-Methyl-3-indolylacetonitrile ($C_{11}H_{10}N_2$ - MW=170.21).

20 cm$^3$ of 50% aqueous sodium hydroxide solution are added to a mixture of 7.8 g (0.05 mol) of 3-indolylacetonitrile, 14.2 g (0.1 mol) of methyl iodide and 0.83 g of a solution of Triton B in methanol at a rate such that the temperature of the reaction mixture does not exceed 35° C. (approximately 1 h 30 min), and the reaction mixture is then stirred for 3 hours at room temperature; thereafter, 100 cm$^3$, of water are added while cooling and the mixture is extracted with diethyl ether, the ether extract is thereafter washed with water to neutrality, dried over sodium sulphate and then filtered, the ether is evaporated off and the residue is crystallised in a sufficient quantity of pentane; the solid thereby obtained is drained and then dried.

M.p. 59°-60° C. Yield=4.1 g=48%.
TLC (SiO$_2$ - hexane/ethyl acetate, 3:1): R$_f$=0.43.
IR $\gamma$CN=2240 cm$^{-1}$
NMR (CDCl$_3$): 3.65 (s,3H); 3.70 (s,2H); 6.9-7.6 (M,5H).

Stage 2

1-(1-Methyl-3-indolyl)cyclopentanecarbonitrile ($C_{15}H_{16}N_2$-MW=224.30).

The reaction is performed under a dry nitrogen atmosphere. A mixture comprising 4.1 g (0.024 mol) of compound of stage 1, 5.7 g (0.024 mol) of 1,4-dibromobutane and 60 cm$^3$ of diethyl ether is added to a suspension of 2.1 g of sodium hydride at a concentration of 60% in oil (0.048 mol+10%), washed beforehand to remove its oil, in 30 cm$^3$ of dimethyl sulphoxide; the rate of this addition is adjusted so as to maintain a gentle reflux of the mixture, which is thereafter maintained under reflux by heating for 4 hours, 150 cm³ of water are then added thereto and the mixture is extracted with diethyl ether, the ether extract is washed with water to neutrality, dried over sodium sulphate and then filtered, the ether is evaporated off and the residue is chromatographed on an alumina column (40 g) using diethyl ether as eluent; the first fraction eluted yields, after evaporation of the ether, a solid which is crystallised by dispersion in pentane; this solid is filtered off and dried.

M.p. 118°–120° C. Yield=2.9 g=54%.

TLC (SiO$_2$ - hexane/ethyl acetate, 3:1): R$_f$=0.5.

IR: $\gamma$CN=2223 cm$^{-1}$.

NMR (CDCl$_3$) 1.8–2.2 (M,4H); 2.2–2.7 (M,4H); 3.7 (s,3H); 6.9–7.8 (M,5H).

Stage 3

1(1-Methyl-3-indolyl)cyclopentylmethylamine (C$_{15}$H$_{20}$N$_2$ -MW=228.33).

The reaction is performed under a dry nitrogen atmosphere. A solution of 2.9 g (0.0129 mol) of compound of stage 2 in 100 cm³ of diethyl ether is added dropwise to 0.73 g (0.0193 mol) of lithium aluminium hydride in 18 cm³ of diethyl ether so as to maintain a gentle reflux of the ether, and the mixture is then heated to reflux for 3 h 30 min; dilute aqueous sodium hydroxide is thereafter added thereto until the lithium/aluminium complex is destroyed, the ether phase is separated after settling has taken place, dried over sodium sulphate and then filtered, and the ether is evaporated off from the filtrate; an oil is thereby obtained, which oil is dissolved in a sufficient quantity of hexane, this solution is filtered, the filtrate is then evaporated and an oil is thereby isolated, which oil is used in the next step of the synthesis without further treatment.

Yield=2.6 g=88%.

TLC (SiO$_2$ - ethyl acetate/dichloromethane/methanol, 4:5:1):1 spread spot.

IR: $\gamma$NH$_2$=3370 and 3390 cm$^{-1}$.

Stage 4

N$^1$-(2,6-Diisopropylphenyl)-N$^2$-[1-(1-methyl-3-indolyl)-cyclopentylmethyl)urea (compound No. 1)

A solution of 2.03 g (0.01 mol) of 2,6-diisopropylphenyl isocyanate in 20 cm³ of hexane is added dropwise to a solution of 2.6 g (0.0144 mol) of compound of stage 3 in 50 cm³ of hexane, and the mixture is stirred for 2 hours at room temperature; the precipitate obtained is thereafter drained, washed with diisopropyl ether and then with pentane and dried.

M.p. 193°–195° C. (diisopropyl ether). Yield=2 g=46%.

IR: $\gamma$CO=1638 cm$^{-1}$.

NMR (CDCl$_3$): 0.9 (d,12H); 1.5–2 (M,8H); 3(hept.,2H); 3.45 (s,3H); 3.2–4 (M,3H); 5.85 (s,1H); 6.2 (s,1H); 6.8–7.6 (M,7H).

| Percentage analysis (C$_{28}$H$_{37}$N$_3$O - MW = 431.60): | | | |
|---|---|---|---|
| | C | H | N |
| % calculated | 77.92 | 8.64 | 9.74 |
| % found | 77.63 | 8.80 | 9.66 |

EXAMPLE 2

N$^1$-[1-(1-Indolyl)cyclopentylmethyl]-N$^2$-(2,6-diisopropylphenyl)urea (compound No. 2, formula 1: R$_1$=R$_2$=R$_3$=R$_4$=R$_5$=H, R$_6$=2,6-diisopropylphenyl, Z=—(CH$_2$)$_n$—C(R$_7$R$_8$)—(CH$_2$)$_p$— at position 1-, n=p=0, R$_7$—R$_8$=—CH$_2$)$_4$—).

Stage 1

1-Indolylacetonitrile (C$_{10}$H$_8$N$_2$ - MW=156.18).

The reaction is performed under a dry nitrogen atmosphere. 23.4 g (0.2 mol) of indole dissolved in 50 cm³ of dimethylformamide are added to a suspension of 8 g of sodium hydride at a concentration of 60% in oil (0.2 mol), washed beforehand to remove its oil, in 150 cm³ of dimethylformamide; the rate of this addition is adjusted so that the temperature of the reaction mixture does not exceed 40° C.; the mixture is thereafter stirred for 1 h at room temperature, and 15.1 g (0.2 mol) of chloroacetonitrile dissolved in 40 cm³ of dimethylformamide are then added dropwise so that the temperature does not exceed 40° C.; the mixture is thereafter stirred for 3 hours at room temperature, 300 cm³ of water are then added thereto, the mixture is extracted with diethyl ether, the ether extract is washed with water to neutrality, dried over sodium sulphate and filtered and the filtrate is evaporated to dryness; a solid is thereby isolated, which solid is dispersed in diisopropyl ether, then filtered off and dried.

M.p. 75°–77° C.

Yield=8.1 g=26%.

TLC (SiO$_2$ - hexane/ethyl acetate, 2:1): R$_f$=0.63.

IR: $\gamma$CN=2245 cm$^{-1}$

NMR (CDCl$_3$): 4.8 (s,2H); 6.52 (d,1H); 6.98 (d,1H); 7.2–7.7 (M,4H).

Stage 2

1-(1-Indolyl)cyclopentanecarbonitrile (C$_{14}$H$_{14}$N$_2$ - MW=210.27)

Prepared from the compound of stage 1 by the process described in stage 2 of Example 1.

Yield=77%.

TLC (SiO$_2$ - hexane/ethyl acetate, 2:1).

IR $\gamma$CN=2237 cm$^{-1}$.

NMR (CDCl$_3$): 1.7–2.1 (M,4H); 2.4–2.9 (M, 4H); 6.45 (d,1H); 7–7.7 (M,5H).

Stage 3

1-(1-Indolyl)cyclopentylmethylamine (C$_{14}$H$_{18}$N$_2$ - MW=214.30)

Prepared from the compound of stage 2 by the process described in stage 3 of Example 1. The compound obtained is used in the crude state.

Yield=81%.

IR $\gamma$NH$_2$=3381 and 3310 cm$^{-1}$.

NMR (CDCl$_3$): 0.9 (s,2H); 1.5–2 (M,4H); 2.6–3.1 (M,4H); 3.05 (s,2H); 6.4 (d,1H); 7–7.8 (M,5H).

Stage 4

N$^1$-[1-(1-Indolyl)cyclopentylmethyl]-N$^2$-(2,6-diisopropylphenyl)urea (compound No. 2)

Prepared from the compound of stage 3 by the process described in stage 4 of Example 1.

M.p. 188°–190° C. Yield=63%.

IR: $\gamma$CO=1637 cm$^{-1}$.

NMR (CDCl$_3$): 1 (d,12H); 1.5–2 (M,4H); 2–2.5 (M,4H); 3(hept.,2H); 3.55 (s,3H); 3.2–4 (broad,1H); 6.05 (d,1H); 6 2 (s,1H); 6.5–7.6 (M,8H).

| Percentage analysis ($C_{27}H_{35}N_3O$ - MW = 417.57): | | | |
|---|---|---|---|
| | C | H | N |
| % calculated | 77.66 | 8.45 | 10.06 |
| % found | 77.50 | 8.66 | 10.01 |

EXAMPLE 3

$N^1$-(2,6-Diisopropylphenyl)-$N^2$-{3-[1-(1-methyl-3-indolyl)-cyclopentyl]propyl}urea (compound No. 3, formula 1: $R_1$=1-$CH_3$, $R_2$=$R_3$=$R_4$=$R_5$=H, $R_6$=2,6-diisopropylphenyl, Z=—$(CH_2)_n$—C($R_7R_8$)—$(CH_2)_p$— at position 3-, n=0, p=2, $R_7$—$R_8$=—$(CH_2)_4$-).

Stage 1

1-(1-Methyl-3-indolyl)cyclopentanecarbaldehyde ($C_{15}H_{17}NO$ - MW=227.30)

The reaction is performed under a dry nitrogen atmosphere. 94.4 cm³ (0.0944 mol) of a 1N toluene solution of diisobutylaluminium hydride are added at −60° C. to a solution of 13.3 g (0.059 mol) of 1-(1-methyl-3-indolyl)-cyclopentanecarbonitrile in 230 cm³ of toluene. The temperature of the mixture is thereafter allowed to rise to room temperature, and the reaction is then stopped by adding 50 cm³ of methanol and then 230 cm³ of 3N hydrochloric acid to the reaction mixture. The mixture is extracted with dichloromethane, the organic extract is washed with water, dried over sodium sulphate and filtered and the filtrate is evaporated. In succession, the residue obtained is taken up with diisopropyl ether, some insoluble matter is removed by filtration, the solvent is evaporated and the residue is crystallised in hexane.

M.p. 69°-70° C. Yield=7.1 g=53%.
IR: $\gamma CO$=1714 cm⁻¹.
NMR (CDCl₃): 1.4-3 (M,8H); 3.7 (s,3H); 6.9 (s,1H); 6.9-7.6 (M,4H); 9.4 (s,1H).

Stage 2

(E/Z)-3-[1-(1-Methyl-3-indolyl)cyclopentyl]-2-propenenitrile ($C_{17}H_{18}N_2$ - MW =250.33).

The reaction is performed under a dry nitrogen atmosphere. 5.3 cm³ (0.033 mol) of diethyl cyanomethylphosphonate are added dropwise at a temperature of between 20° and 25° C. (cooling in an ice bath) to a suspension of 1.4 g (0.033 mol +5%) of sodium hydride, in 60% suspension in oil, in 40 cm³ of tetrahydrofuran. The mixture is thereafter stirred for 1 hour at room temperature, 7.5 g (0.033 mol) of compound of stage 1 dissolved in 40 cm³ of tetrahydrofuran are then added thereto, and the mixture is stirred for a further hour and then heated to reflux for 2.5 hours. After cooling of the reaction mixture, in succession, ice-cold water is added thereto, the mixture is extracted with ethyl ether, the ether extract is washed with water, dried over sodium sulphate and filtered, the filtrate is evaporated and the residue is crystallised in hexane.

M.p. 57°-59° C. Yield=6 g=73%.
NMR (CDCl₃): 1.5-2.5 (M,8H); 3.7 (s,3H); 4.95-5.1 (d,J=16.5,J =1 2,1H); 6.6-7.7 (M,6H).

Stage 3

3-[1-(1-Methyl-3-indolyl)cyclopentyl]propylamine ($C_{17}H_{24}N_2$ - MW=250.33)

2.50 g (0.01 mol) of compound of stage 2 dissolved in 70 cm³ of ethanol saturated beforehand with ammonia are hydrogenated under pressure and in the presence of 2 g of Raney nickel. After 5 hours of heating at 70° C., the mixture is filtered and the filtrate is evaporated to dryness.

Oil. Yield=2.1 g=84%.
TLC (SiO₂ - dichloromethane/methanol, 4:1).
IR: $\gamma NH$:=2360 cm⁻¹.
NMR (CDCl₃): 0.8-3 (M,16H); 3.6 (s,3H); 6.7 (s,1H); 6.8-7.6 (M,4H).

Stage 4

$N^1$-(2,6-Diisopropylphenyl)-$N^2$-{3-[1-(1-methyl-3-indolyl)-cyclopentyl]propyl}urea (compound No. 3)

A solution of 5.25 g (0.02 mol +5%) of compound of stage 3 and 6.45 g (0.02 mol) of 2,2,2-trichloro-N-(2,6-diisopropylphenyl)acetamide in 30 cm³ of N,N-dimethylformamide is heated to 110° C. for 30 minutes in the presence of 8.3 g (0.06 mol) of potassium carbonate. After cooling, 200 cm³ of cold water are added to the reaction mixture and the precipitate formed is drained, washed with water and then dried. The product is recrystallised in ethanol.

M.p. 194°-196° C. Yield=6.89 g=75%.
IR: $\gamma CO$=1634 cm⁻¹.
NMR (DMSO-d₆): 1.1 (d,12H); 1.5-2.2 (M,12H); 2.7-3.4 (M,4H); 3.25 (s,1H); 3,7 (s,3H); 5.75 (broad, 1H); 6.8-7.8 (M,8H).

| Percentage analysis ($C_{30}H_{41}N_3O$ - MW = 459.68): | | | |
|---|---|---|---|
| | C | H | N |
| % calculated | 78.39 | 8.99 | 9.14 |
| % found | 78.30 | 8.94 | 9.11 |

EXAMPLE 4

$N^1$-(2,6-Diisopropylphenyl)-$N^2$-{2-[1-(1-methyl-3-indolyl)-cyclopentyl]ethyl}urea (compound No. 4, formula 1: $R_1$=1-$CH_3$, $R_2$=$R_3$=$R_4$=$R_5$=H, $R_6$=2,6-diisopropylphenyl, Z=—$(CH_2)_n$—C($R_7R_8$)—$(CH_2)_p$— at position 3-, n=0, p=1, $R_7$-$R_8$=—$(CH_2)_4$—).

Stage 1

1-(1-Methyl-3-indolyl)cyclopentaneacetonitrile ($C_{16}H_{19}N_2$-MW=238.32)

2.9 g (0.0134 mol) of 1-(1-methyl-3-indolyl)-cyclopentanecarbaldehyde and 5 g (0.0166 mol) of 2,4,6-triisopropylbenzenesulphonohydrazide dissolved in 30 cm³ of tetrahydrofuran are stirred at room temperature for 3 hours. The tetrahydrofuran is thereafter evaporated off completely and 2.6 g (0.0402 mol) of potassium cyanide and 30 cm³ of methanol are added to the residue. The mixture is heated to reflux for 4.5 hours and then cooled, water is added and the mixture is extracted with dichloromethane. In succession, the organic extract obtained is washed with aqueous sodium hydrogen carbonate solution, dried over sodium sulphate and filtered and the solvent is evaporated off. The crude product thereby isolated is purified by chromatography on a silica gel column in dichloromethane and then, where appropriate, by flash chromatography using a 3:1 hexane/ethyl acetate mixture as eluent.

Oil. Yield=0.8 g=25%.
IR: $\gamma CN$=2250 cm⁻¹.
NMR (CDCl₃): 1.5-2.7 (M,8H); 2.8 (s,2H); 3.7 (s,3H); 6.8-8 (M,5H).

Stage 2

2-[1-(1-Methyl-3-indolyl)cyclopentyl]ethylamine ($C_{16}H_{22}N_2$ - MW=242.36)

Prepared by reduction of the compound of stage 1 with lithium aluminium hydride exactly according to the process of stage 3 of Example 1.
Oil. Yield=74%.

Stage 3

$N^1$-(2,6-Diisopropylphenyl)-$N^2$-{2-[1-(1-methyl-3-indolyl)-cyclopentyl]ethyl}urea (compound No. 4)

Prepared by condensation of 2,6-diisopropylphenyl isocyanate with the compound of stage 2 under the conditions of Example 1.
M.p.=239°-241° C. (acetone). Yield=25%.
IR: $\gamma NH=3145, 3252$ cm$^{-1}$; $\gamma CO=1647$ cm$^{-1}$.

| Percentage analysis ($C_{29}H_{39}N_3O$ - MW = 445.65): | | | |
|---|---|---|---|
| | C | H | N |
| % calculated | 78.16 | 8.82 | 9.43 |
| % found | 77.85 | 8.92 | 9.20 |

EXAMPLE 5

$N^1$-Benzyl-$N^2$-(2,6-diisopropylphenyl)-$N^1$-[1-(1-methyl-3-indolyl)cyclopentylmethyl]urea (compound No. 5, formula 1: $R_1$=1—$CH_3$, $R_2$=$R_3$=$R_4$=H, $R_5$=$C_6H_5CH_2$, $R_6$=2,6-diisopropylphenyl, Z=—$(CH_2)_n$—$C(R_7R_8)$—$(CH_2)_p$— at position 3-, n=p=0, $R_7$-$R_8$=-$(CH_2)_4$-).

Stage 1

N-[1-(1-Methyl-3-indolyl)cyclopentylmethyl]benzamide ($C_{22}H_{24}N_2O$ - MW=332.45)

The reaction is performed under a dry nitrogen atmosphere. 9.8 g (0.07 mol) of benzoyl chloride dissolved in 70 cm$^3$ of diethyl ether are added dropwise to a solution of 16 g (0.07 mol) of 1-(1-methyl-3-indolyl)-cyclopentylmethylamine and 7.08 g (0.07 mol) of triethylamine in 70 cm$^3$ of diethyl ether so as to maintain a gentle reflux of the ether, and the mixture is then stirred for 2 hours at room temperature. The precipitate formed is thereafter drained, the ether solution is washed with water, dried over sodium sulphate and filtered and the ether is evaporated off from the filtrate. The residue thereby obtained is crystallised by washing with cold diisopropyl ether.
M.p.=109°-111° C. Yield=87%.
TLC ($SiO_2$ - hexane/ethyl acetate, 2:1): $R_f$=0.45.
IR: $\gamma NH=3340-3324$ cm$^{-1}$; $\gamma CO=1640$ cm$^{-1}$.

Stage 2

N-Benzyl-N-[1-(1-methyl-3-indolyl)cyclopentylmethyl]amine ($C_{22}H_{26}N_2$ - MW=318.46)

The reaction is performed under a dry nitrogen atmosphere. 20.2 g (0.0607 mol) of the compound of stage 1 dissolved in 250 cm$^3$ of a 1:1 mixture of diethyl ether and tetrahydrofuran are added dropwise to 4.6 g (0.0607 mol) of lithium aluminium hydride suspended in 125 cm$^3$ of diethyl ether so as to maintain a gentle reflux of the ether. The mixture is heated to reflux for 42 hours. After 8 hours of heating under reflux, the ether is replaced by tetrahydrofuran. On completion of the heating, the mixture is cooled to 20° C, and a sufficient quantity of dilute aqueous sodium hydroxide is added thereto to destroy the lithium/aluminium complex. The precipitate formed is drained and washed with ether, which is combined with the filtrate, and the solvents are evaporated off completely from the filtrate.
Oil. Yield=75%.
TLC ($SiO_2$ - hexane/ethyl acetate, 1:1): $R_f$=0.40.
NMR (CDCl$_3$): 1.2 (broad,1H); 1.5–2.2 (M,8H); 2.8 (s,2H); 3.6 (s,2H); 3.65 (s,3H); 6.8–7.7 (M,10H).

Stage 3

$N^1$-Benzyl-$N^2$-(2,6-diisopropylphenyl)-$N^1$-[1-(1-methyl-3-indolyl)cyclopentylmethyl]urea (compound No. 5)

Prepared from the compound of stage 2 and 2,6-diisopropylphenyl isocyanate exactly according to the process described in stage 4 of Example 1.
M.p. 101°-103° C. (diisopropyl ether). Yield=66%.
TLC ($SiO_2$ - hexane/ethyl acetate, 2:1): $R_f$=0.70.
NMR (CDCl$_3$): 0.9–1.2 (M,12H); 1.5–2.3 (M,8H); 2.8 (hept.,2H); 3.7 (s,3H); 3.9 (s,2H); 3.95 (s,2H); 5.4 (broad,1H); 6.8 (s,1H); 7–7.9 (M,12H).

| Percentage analysis ($C_{35}H_{43}N_3O$ - MW = 521.75): | | | |
|---|---|---|---|
| | C | H | N |
| % calculated | 80.57 | 8.31 | 8.05 |
| % found | 80.71 | 8.43 | 7.99 |

EXAMPLE 6

Using the appropriate processes of Examples 1 to 5, the compounds (see Table 1 below) of general formula 1 in which $R_2$=$R_4$'$R_5$=H, Z=-$(CH_2)_n$C($R_7R_8$)-$(CH_2)_p$- at position 3- and n=p=0 were prepared.

The meanings of the abbreviations used in Tables 1 to 3 below are as follows: Me=$CH_3$—, iPr=$(CH_3)_2CH$—, Et=$CH_3CH_2$—, allyl=$CH_2$=$CH$—$CH_2$—, n-Bu=n-$C_4H_9$—, DMAE=$(CH_3)_2N$—$CH_2CH_2$—, 4F—Bn= 4F—$C_6H_4CH_2$—, pyrim=pyrimidinyl, MeO=$CH_3O$—, iPrO=$(CH_3)_2CHO$, pyr=pyridyl.

TABLE 1

| Compound No. | $R_1$ | $R_3$ | $R_6$ | $R_7$ | $R_8$ | M.p. °C. |
|---|---|---|---|---|---|---|
| 6 | 1-Me | H | $C_6H_5$ | —$(CH_2)_4$— | | 214–216 |
| 7 | H | H | 2,6-iPr$_2$C$_6$H$_3$ | H | H | 160–162 |
| 8 | 1-Me | H | 2,4-F$_2$C$_6$H$_3$ | —$(CH_2)_4$— | | 226–228 |
| 9 | 1-Me | H | 2,6-iPr$_2$C$_6$H$_3$ | iPr | H | 155–157 |
| 10 | 1-Me | H | C(Me)$_3$ | —$(CH_2)_4$— | | 214–216 |
| 11 | 1-Me | H | 2,6-iPr$_2$C$_6$H$_3$ | Me | H | 207–209 |
| 12 | 1-CH$_2$C$_6$H$_5$ | H | 2,6-iPr$_2$C$_6$H$_3$ | —$(CH_2)_4$— | | 83–86 |
| 13 | 1-Et | H | 2,6-iPr$_2$C$_6$H$_3$ | —$(CH_2)_4$— | | 166–168 |
| 14 | 1-Me | H | 2,6-iPr$_2$C$_6$H$_3$ | Et | H | 159–161 |
| 15 | 1-Me | 5-Me | 2,6-iPr$_2$C$_6$H$_3$ | —$(CH_2)_4$— | | 188–190 |
| 16 | 1-Me | H | 2,6-iPr$_2$C$_6$H$_3$ | —$(CH_2)_5$— | | 187–189 |

TABLE 1-continued

| Compound No. | $R_1$ | $R_3$ | $R_6$ | $R_7$ | $R_8$ | M.p. °C. |
|---|---|---|---|---|---|---|
| 17 | 1-Me | H | 2,6-iPr$_2$C$_6$H$_3$ | Et | Et | 183–184 |
| 18 | 1-Me | H | 2,6-iPr$_2$C$_6$H$_3$ | Me | Me | 172–174 |
| 19 | 1-iPr | H | 2,6-iPr$_2$C$_6$H$_3$ | —(CH$_2$)$_4$— | | 168–170 |
| 20 | 1-allyl | H | 2,6-iPr$_2$C$_6$H$_3$ | —(CH$_2$)$_4$— | | 131–133 |
| 21 | 1-Me | H | 2,6-iPr$_2$C$_6$H$_3$ | C$_6$H$_5$ | H | 168–170 |
| 22 | 1-Me | H | 2,6-iPr$_2$C$_6$H$_3$ | allyl | allyl | 121–123 |
| 23 | 1-C$_6$H$_5$ | H | 2,6-iPr$_2$C$_6$H$_3$ | —(CH$_2$)$_4$— | | 121–123 |
| 24 | 1-Me | H | 2,6-iPr$_2$C$_6$H$_3$ | —(CH$_2$)$_3$— | | 201–203 |
| 25 | 1-Me | H | 2,6-iPr$_2$C$_6$H$_3$ | n-Bu | n-Bu | 93–96 |
| 26 | 1-Me | H | 2,6-iPr$_2$C$_6$H$_3$ | allyl | H | 148–150 |
| 27 | 1-n-C$_7$H$_{15}$ | H | 2,6-iPr$_2$C$_6$H$_3$ | —(CH$_2$)$_4$— | | 74–80 |
| 28 | 1-n-C$_4$H$_9$ | H | 2,6-iPr$_2$C$_6$H$_3$ | —(CH$_2$)$_4$— | | 128–130 |
| 29 | 1-Me | H | 2,6-iPr$_2$C$_6$H$_3$ | n-C$_4$H$_9$ | H | 143–145 |
| 30 | 1-Me | H | 2,6-iPr$_2$C$_6$H$_3$ | n-C$_7$H$_{15}$ | H | 120–122 |
| 31 | 1-Me | H | 2,6-iPr$_2$C$_6$H$_3$ | (CH$_3$)$_3$CCH$_2$ | H | 145–160 |
| 32 | 1-Me | H | 2,6-iPr$_2$C$_6$H$_3$ | C$_6$H$_5$CH$_2$ | H | 158–160 |
| 33 | 1-Me | H | 2,6-Cl$_2$C$_6$H$_3$ | —(CH$_2$)$_4$— | | 199–201 |
| 34 | 1-Me | H | 2,6-iPr$_2$C$_6$H$_3$ | —(CH$_2$)$_6$— | | 182–184 |
| 35 | 1-Me | H | 2,6-iPr$_2$C$_6$H$_3$ | —(CH$_2$)$_2$O(CH$_2$)$_2$— | | 197–201 |
| 36 | 1-Me | H | 2,6-Et$_2$C$_6$H$_3$ | —(CH$_2$)$_4$— | | 171–173 |
| 37 | 1-DMAE | H | 2,6-iPr$_2$C$_6$H$_3$ | —(CH$_2$)$_4$— | | 132–136 |
| 38 | 1-(4F-Bn) | H | 2,6-iPr$_2$C$_6$H$_3$ | —(CH$_2$)$_4$— | | 68–74 |
| 39 | 1-Me | H | 2,4,6-MeO$_3$C$_6$H$_2$ | —(CH$_2$)$_4$— | | 176–178 |
| 40 | 1-Me | H | 4,6-MeO$_2$-5-pyrim | —(CH$_2$)$_4$— | | 220–222 |
| 41 | 1-Me | 5-MeO | 2,6-iPr$_2$C$_6$H$_3$ | —(CH$_2$)$_4$— | | 157–160 |
| 42 | 1-Me | H | 2,6-iPr$_2$C$_6$H$_3$ | DMAE | H | 172–173 |
| 43 | 1-Me | H | 2,6-iPr$_2$C$_6$H$_3$ | $\mathrm{CH_3\!\!-\!\!C(CH_3)\!\!=\!\!CH_2}$ | H | 148–150 |
| 44 | 1-Me | H | 2,6-iPrO$_2$C$_6$H$_3$ | —(CH$_2$)$_4$— | | 145–147 |
| 45 | 1-(3-pyr-CH$_2$) | H | 2,6-iPr$_2$C$_6$H$_3$ | —(CH$_2$)$_4$— | | 123–124 |

EXAMPLE 7

Using the appropriate processes of Examples 1 to 5, the compounds listed in Table 2 below, of general formula 1 in which $R_1$=1—Me, $R_1$=$R_2$=$R_3$=H, Z = —(CH$_2$)$_n$—C(R$_7$R$_8$)-(CH$_2$)$_9$— at position 3-, n=p=0, R$_7$-R$_8$=—(CH$_2$)$_4$—, were prepared.

TABLE NO. 2

| Compound No. | $R_5$ | $R_6$ | M.p. °C. |
|---|---|---|---|
| 46 | C$_6$H$_5$CH$_2$ | 2,6-Me$_2$C$_6$H$_3$ | 185–187 |
| 47 | C$_6$H$_5$CH$_2$ | 2,6-Cl$_2$C$_6$H$_3$ | 200–202 |
| 48 | C$_6$H$_5$CH$_2$ | 3,4-F$_2$C$_6$H$_3$ | 134–136 |
| 49 | CH$_3$ | 2,6-iPr$_2$C$_6$H$_3$ | 186–188 |

EXAMPLE 8

Using the appropriate processes of Examples 1 to 5, the compounds (see Table 3 below) of formula 1 in which $R_1$=1—Me, $R_3$=$R_4$=$R_5$=H, $R_6$=2,6-diisopropylphenyl, Z=—(CH$_2$)$_n$—C(R$_7$R$_8$)—(CH$_2$)$_p$—, n=p=0, R$_7$—R$_8$=—(CH$_2$)$_4$— were prepared.

TABLE NO. 3

| Compound No. | $R_2$ | Position of Z | M.p. °C. |
|---|---|---|---|
| 50 | 2-Me | 3 | 211–213 |
| 51 | 2-C$_6$H$_5$ | 3 | 210–214 |
| 52 | 3-Me | 2 | 206–208 |

EXAMPLE 9

(-)-N$^1$-(2,6-Diisopropylphenyl)-N$^2$-[2-(1-methyl-3-indolyl)-hexyl]urea (compound No. 53, formula 1: $R_1$=1—CH$_3$, $R_2$=$R_3$=$R_4$=H, $R_6$=2,6-diisopropylphenyl, Z=—(CH$_2$)$_n$—C(R$_7$R$_8$)-(CH$_2$)$_p$— at position 3=, n=p=0, R$_7$=n—C$_4$H$_9$—, R$_8$=H—laevorotatory enantiomer).

Stage 1

(-)-2-(1-Methyl-3-indolyl)hexylamine (-)-mandelate (C$_{23}$H$_{30}$N$_2$O$_3$ - MW=382.50).

24 g (0.104 mol) of 2-(1-methyl-3-indolyl)hexylamine, prepared under the conditions of Example 1, and 15.8 g (0.104 mol) of (R)-(-)-mandelic acid are dissolved in 600 cm$^3$ of ether; after 3 hours of stirring at 20° C., the solid formed is drained and dried (m.p. 92°–100° C., quantity=23.1 g).

The mother liquors are retained for preparing the corresponding dextrorotatory enantiomer as described in Example 10.

The solid obtained above is recrystallised twice in succession in a sufficient quantity of ethyl acetate; a white solid is thereby isolated.

M.p. 115°–116° C. Yield=15.1%.
IR: $\gamma CO_2^- = 1635$ cm$^{-1}$.

Stage 2

(-)-2-(1-Methyl-3-indolyl)hexylamine (C$_{15}$H$_{22}$N$_2$—MW=230.35)

6.7 g (0.0175 mol) of compound of stage 1 are alkalinised with 2N aqueous sodium hydroxide solution; the mixture is extracted with ether (2×25 cm$^3$), the ether extract is dried over sodium sulphate and filtered and the solvent is then evaporated off; a colourless oil is thereby isolated.

Yield=96.8%.

The enantiomeric excess (e.e) is measured by HPLC analysis of the condensation product with (S)-(-)-α-methylbenzyl isocyanate according to the process described in stage 4 of Example 1: e.e.=98%.
$[\alpha]_D^{20} = -9.7°$ (c=3.5; $CH_2Cl_2$).
IR: $\gamma NH_2 = 3369$ and 3297 cm$^{-1}$.
NMR (CDCl$_3$): 0.5-2.2 (M,3H); 1-2 (M,6H); 1.1 (s,2H); 2.85 (ps, 3H); 3.6 (s,3H); 6.7 (s,1H); 6.8-7.6 (M,4H).

Stage 3

(-)-N$^1$-(2,6-Diisopropylphenyl)-N$^2$-[2-(1-methyl-3-indolyl)-hexyl]urea (compound No. 53)

Prepared from the compound of stage 2 by the process described in stage 4 of Example 1, replacing hexane by diisopropyl ether.
M.p. 138°-142° (diisopropyl ether/ethyl acetate, 3:1).
Yield=86.7%.
e.e.=98%.
$[\alpha]_D^{20}$ 32 $-23°$ (c=3; CHCl$_3$).
IR: $\gamma NH = 3383$ and 3279 cm$^{-1}$.
NMR (CDCl$_3$): 0.5-2.2 (M,21H); 2.4-3.5 (M,5H); 3.55 (s,3H); 4 (broad, 1H); 5.7 (s,1H); 6.4 (s,1H); 6.6-7.6 (M,7H).

| Percentage analysis ($C_{28}H_{39}N_3O$ - MW = 433.64): | | | |
|---|---|---|---|
| | C | H | N |
| % calculated | 77.55 | 9.06 | 9.69 |
| % found | 77.86 | 9.22 | 9.67 |

EXAMPLE 10

(+)-N$^1$-(2,6-Diisopropylphenyl)-N$^2$-[2-(1-methyl-3-indolyl)hexyl]urea (compound No. 54, formula 1: $R_1$=1—CH$_3$, $R_2$=$R_3$=$R_4$=H, $R_6$=2,6-diisopropylphenyl, Z=—(CH$_2$)$_n$—C($R_7R_8$)-(CH$_2$)$_p$— at position 3-, n=p=0, $R_7$=n-C$_4$H$_9$-, $R_8$=H - dextrorotatory enantiomer).

Stage 1

(+)-2-(1-Methyl-3-indolyl)hexylamine (+)-mandelate ($C_{23}H_{30}N_2O_3$ - MW=382.50)

The mother liquors obtained in stage 1 of Example 9 are alkalinised according to the process described in stage 2 of the same example; the amine isolated according to this process is thereafter salified with (S)-(+)-mandelic acid according to the process described in stage 1 of Example 9; a solid is thereby isolated, which solid is recrystallised successively in a 7:3 diisopropyl ether/ethyl acetate mixture, and then twice in ethyl acetate to which a sufficient quantity of ether for obtaining the expected separation has been added.
A white solid is thereby isolated.
M.p. 112°-114° C. Yield=29.5%.
IR: $\gamma CO_2^- = 1635$ cm$^{-1}$.

Stage 2

(+)-2-(1-Methyl-3-indolyl)hexylamine ($C_{15}H_{22}N_2$ - MW=230.35)

Prepared from the compound of stage 1 according to the process described in stage 2 of Example 9.

A colourless oil is thereby isolated. Yield=99.3%.
The enantiomeric excess (e.e.) is measured by HPLC analysis of the condensation product with (S)-(-)-α-methylbenzyl isocyanate, obtained by the process described in stage 3 of Example 9: e.e. =99.6%.
$[\alpha]_D^{20} = +10.3°$ (c=3.5; $CH_2Cl_2$).
IR: $\gamma NH_2 = 3373$ and 3297 c$^{-1}$.
NMR (CDCl$_3$): 0.6-1 (M,3H); 1-2 (M,6H); 1.4 (s,2H); 2.9 (ps,3H); 3.6 (s,3H); 6.75 (s,1H); 6.8-7.7 (m,4H).

Stage 3

(+)-N$^1$-(2,6-diisopropylphenyl)-N$^2$-[2-(1-methyl-3-indolyl)hexyl]urea (compound No. 54)

Prepared from the compound of stage 2 by the process described in stage 4 of Example 1, using diisopropyl ether in place of hexane.
A white solid is thereby isolated.
M.p. 132°-140° C. (diisopropyl ether/ethyl acetate, 3:1).
e.e.=99.6%.
$[\alpha]_D^{20} = +23.6°$ (c=3; CHCl$_3$).
IR: $\gamma NH = 3383$ and 3278 cm$^{-1}$; $\gamma CO = 1644$ cm$^{-1}$.
NMR (CDCl$_3$): 0.5-2.2 (M,21H); 2.4-3.5 (M,5H); 3.55 (s,3H); 4 (broad,1H); 5.7 (s,1H); 6.4 (s,1H); 6.6-7.6 (M,7H).

| Percentage analysis ($C_{28}H_{39}N_3O$ - MW = 433.64): | | | |
|---|---|---|---|
| | C | H | N |
| % calculated | 77.55 | 9.06 | 9.69 |
| % found | 77.53 | 9.10 | 9.82 |

EXAMPLE 11

Intermediate compounds of general formula 6 in which Z=—(CH$_2$)$_n$—C($R_7R_8$)—(CH$_2$)$_p$— at position 3-, n=p=0 and $R_2$=$R_4$=$R_7$=$R_8$=H (Table No. 4):

TABLE NO. 4

| Compound No. | $R_1$ | $R_3$ | M.p. °C. B.p./mm |
|---|---|---|---|
| 55 | 1-CH$_2$C$_6$H$_5$ | H | 89-90 |
| 56 | 1-Et | H | oil |
| 57 | 1-Me | 5-Me | oil |
| 58 | 1-iPr | H | 59-61 |
| 59 | 1-allyl | H | 145-150/0,2 |
| 60 | 1-C$_6$H$_5$ | H | oil |
| 61 | 1-n-C$_7$H$_{15}$ | H | oil |
| 62 | 1-n-C$_4$H$_9$ | H | oil |
| 63 | 1-DMAE | H | oil |
| 64 | 1-(4F-Bn) | H | 94-96 |
| 65 | 1-Me | 5-MeO | 104-106 |
| 66 | 1-(3-pyr-CH$_2$) | H | 88-90 |

EXAMPLE 12

Intermediate compounds of general formula 6 in which Z=—(CH$_2$)$_n$—C($R_7R_8$)—(CH$_2$)$_p$— at position 3—, n=p=0 and $R_2$=$R_4$=H (Table No. 5):

TABLE 5

| Compound No. | $R_1$ | $R_3$ | $R_7$ | $R_8$ | M.p. °C. |
|---|---|---|---|---|---|
| 67 | 1-Me | H | iPr | H | 80-81 |
| 68 | 1-Me | H | Me | H | 61-64 |
| 69 | 1-CH$_2$C$_6$H$_5$ | H | —(CH$_2$)$_4$— | | 144-146 |
| 70 | 1-Et | H | —(CH$_2$)$_4$— | | 76-78 |
| 71 | 1-Me | H | Et | H | oil |

TABLE 5-continued

| Compound No. | R₁ | R₃ | R₇ | R₈ | M.p. °C. |
|---|---|---|---|---|---|
| 72 | 1-Me | 5-Me | —(CH₂)₄— | | amorphous |
| 73 | 1-Me | H | —(CH₂)₅— | | 128–130 |
| 74 | 1-Me | H | Et | Et | 58–60 |
| 75 | 1-Me | H | Me | Me | 44–46 |
| 76 | 1-iPr | H | —(CH₂)₄— | | 69–71 |
| 77 | 1-allyl | H | —(CH₂)₄— | | 58–60 |
| 78 | 1-Me | H | allyl | allyl | 76–79 |
| 79 | 1-C₆H₅ | H | —(CH₂)₄— | | oil |
| 80 | 1-Me | H | —(CH₂)₃— | | 98–100 |
| 81 | 1-Me | H | n.C₄H₉ | n.C₄H₉ | 73–75 |
| 82 | 1-Me | H | allyl | H | 60–62 |
| 83 | 1-n-C₇H₁₅ | H | —(CH₂)₄— | | oil |
| 84 | 1-n-C₄H₉ | H | —(CH₂)₄— | | oil |
| 85 | 1-Me | H | n.C₄H₉ | H | 63–66 |
| 86 | 1-Me | H | n.C₇H₁₅ | H | 43–45 |
| 87 | 1-Me | H | —(CH₂)₆— | | 99–101 |
| 88 | 1-Me | H | —(CH₂)₂O(CH₂)₂— | | 178–180 |
| 89 | 1-DMAE | H | —(CH₂)₄— | | 56–58 |
| 90 | 1-(4F-Bn) | H | —(CH₂)₄— | | 79–81 |
| 91 | 1-Me | 5-MeO | —(CH₂)₄— | | 100–101 |
| 92 | 1-Me | H | DMAE | H | oil |
| 93 | 1-Me | H | CH₃\C=CH₂/CH₃ | H | oil |
| 94 | 1-(3-pyr-CH₂) | H | —(CH₂)₄— | | 130–132 |

EXAMPLE 13

Intermediate compounds of general formula 6 in which Z=—(CH₂)ₙ—C(R₇R₈)—(CH₂)ₚ—, n=p=0, R₁=1—Me, R₃=R₄=H and R₇—R₈=—(CH₂)₄— (Table No. 6):

TABLE NO. 6

| Compound No. | R₂ | Position of Z | M.p. °C. |
|---|---|---|---|
| 95 | 2-Me | 3 | amorphous |
| 96 | 2-C₆H₅ | 3 | 150–152 |
| 97 | 3-Me | 2 | 135–137 |

EXAMPLE 14

Intermediate compounds of general formula 5 in which Z=—(CH₂)ₙ—C(R₇R₈)—(CH₂)ₚ—, n=p=0, R₁=1—Me, R₃=R₄=H and R₇—R₈=—(CH₂)₄— (Table No. 7):

| Compound No. | R₂ | Position of Z | M.p. °C. | νNH₂ (cm⁻¹) |
|---|---|---|---|---|
| 98 | 2-Me | 3 | amorphous | 3370 |
| 99 | 2-C₆H₅ | 3 | 150–152 | 3380 |
| 100 | 3-Me | 2 | 135–137 | 3377 |

EXAMPLE 15

Intermediate compounds of general formula 5 in which Z=—(CH₂)ₙ—C(R₇R₈)—(CH₂)ₚ— at position 3—, n=p=0 and R₂=R₄=H (Table No. 8):

| Compound No. | R₁ | R₃ | R₇ | R₈ | M.p. °C. | νNH₂ (cm⁻¹) |
|---|---|---|---|---|---|---|
| 101 | 1-Me | H | iPr | H | oil | 3380, 3300 |
| 102 | 1-Me | H | Me | H | oil | 3380 |
| 103 | 1-CH₂C₆H₅ | H | —(CH₂)₄— | | oil | 3360 |
| 104 | 1-Et | H | —(CH₂)₄— | | oil | 3374 |
| 105 | 1-Me | H | Et | H | oil | 3380 |
| 106 | 1-Me | 5-Me | —(CH₂)₄— | | oil | 3370 |
| 107 | 1-Me | H | —(CH₂)₅— | | oil | 3376 |
| 108 | 1-Me | H | Et | Et | oil | 3286 |
| 109 | 1-Me | H | Me | Me | oil | 3380, 3300 |
| 110 | 1-iPr | H | —(CH₂)₄— | | oil | 3377 |
| 111 | 1-allyl | H | —(CH₂)₄— | | oil | 3360 |
| 112 | 1-Me | H | allyl | allyl | oil | 3390 |
| 113 | 1-C₆H₅ | H | —(CH₂)₄— | | oil | 3360 |
| 114 | 1-Me | H | —(CH₂)₃— | | oil | 3380 |

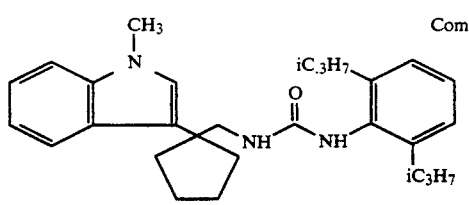

Compound No. 1

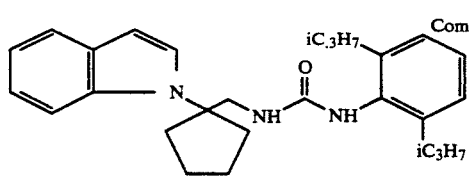

Compound No. 2

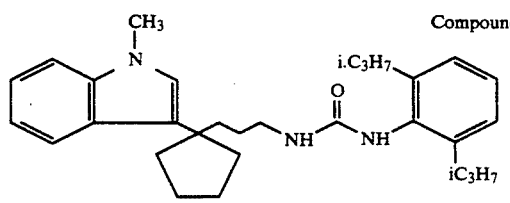

Compound No. 3

-continued
Compound No. 4
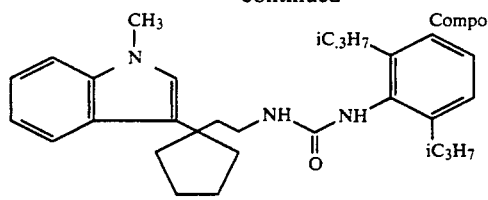
Compound No. 5
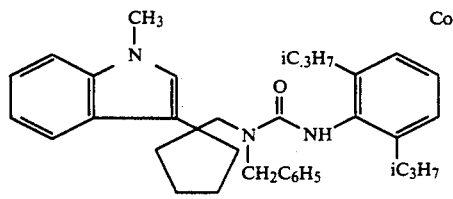
Compound No. 6
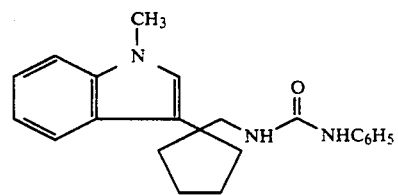
Compound No. 7
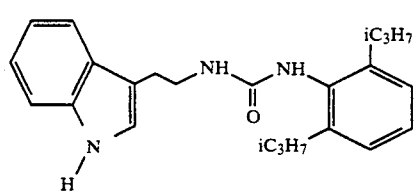
Compound No. 8
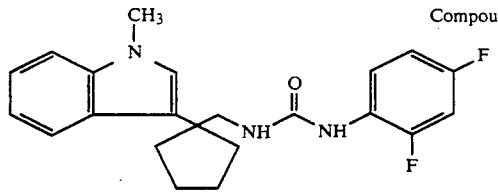
Compound No. 9
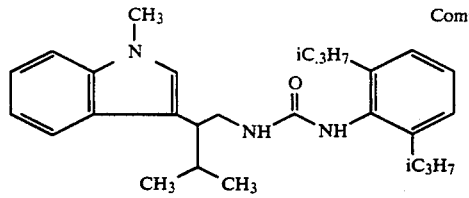
Compound No. 10
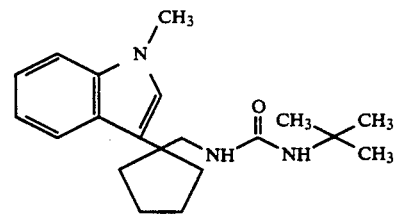
Compound No. 11
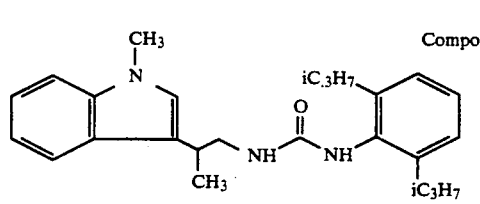
-continued
Compound No. 12
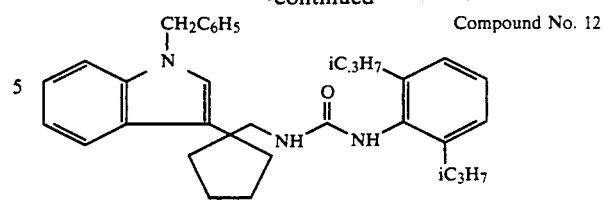
Compound No. 13
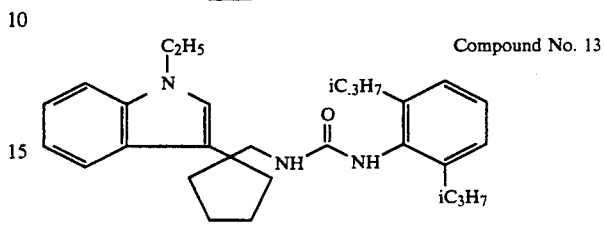
Compound No. 14
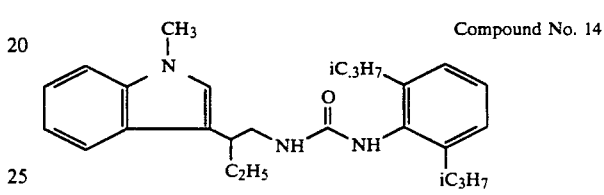
Compound No. 15
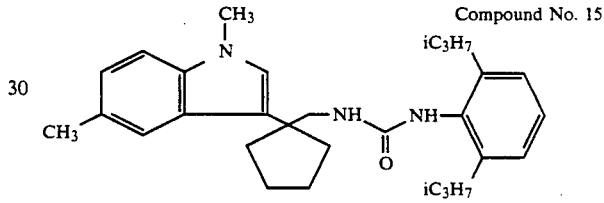
Compound No. 16
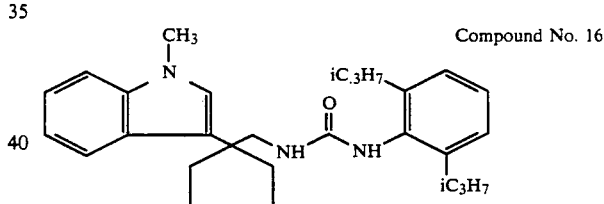
Compound No. 17
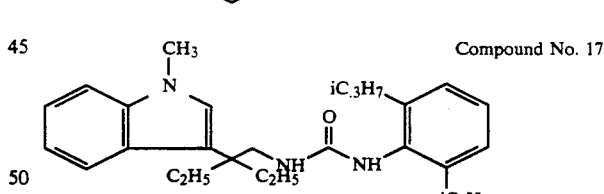
Compound No. 18
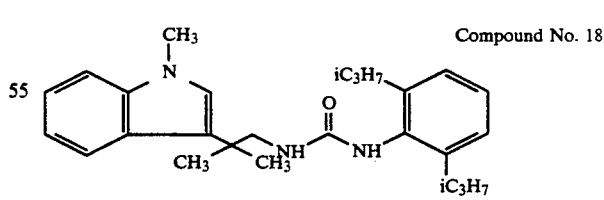
Compound No. 19
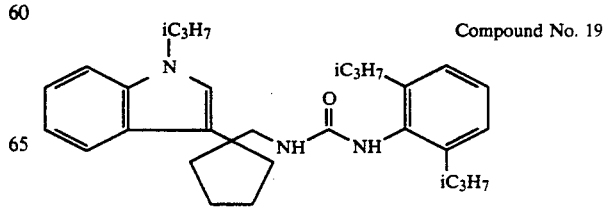

-continued

Compound No. 20
Compound No. 21
Compound No. 22
Compound No. 23
Compound No. 24
Compound No. 25
Compound No. 26

-continued

Compound No. 27
Compound No. 28
Compound No. 29
Compound No. 30
Compound No. 31
Compound No. 32
Compound No. 33

5,219,859
35
-continued
Compound No. 34
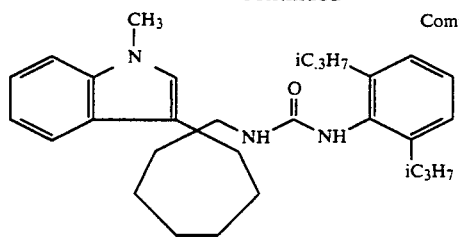
Compound No. 35
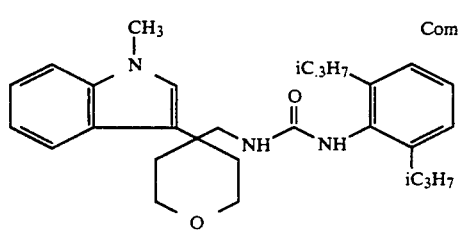
Compound No. 36
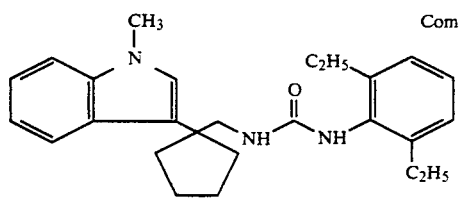
Compound No. 37
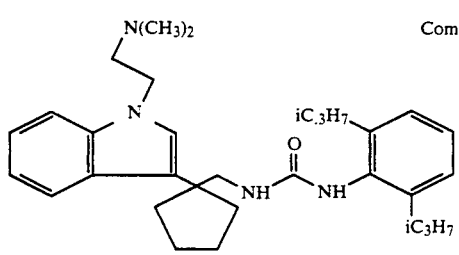
Compound No. 38
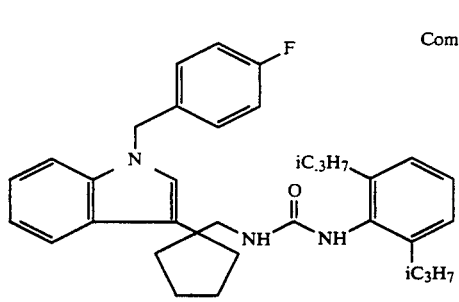
Compound No. 39
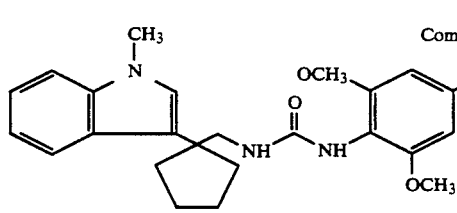
Compound No. 40
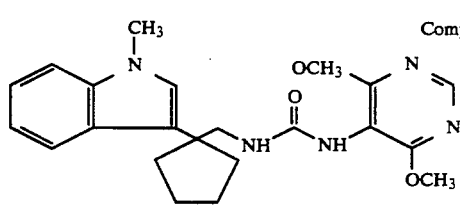
36
-continued
Compound No. 41
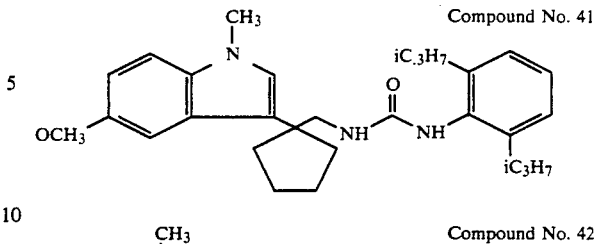
Compound No. 42
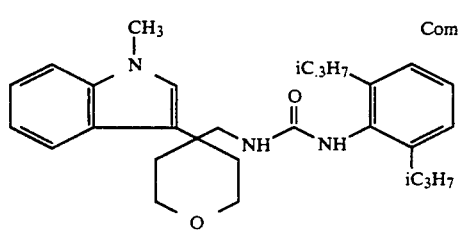
Compound No. 43
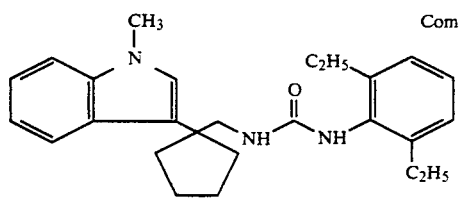
Compound No. 44
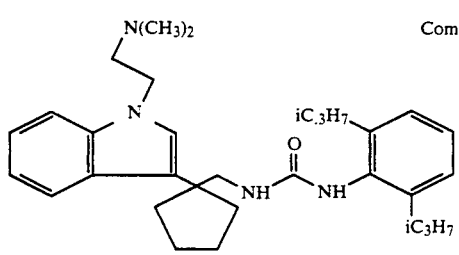
Compound No. 45
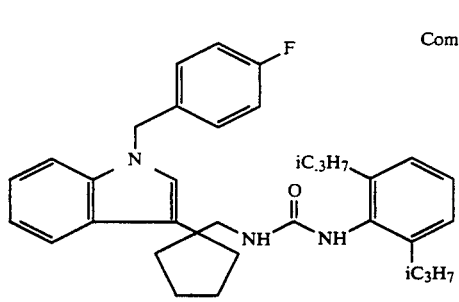
Compound No. 46
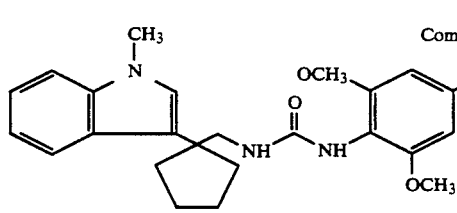
Compound No. 47
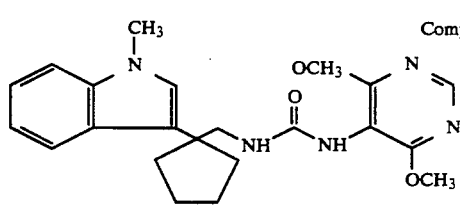

-continued

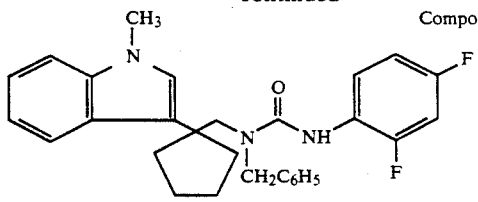
Compound No. 48

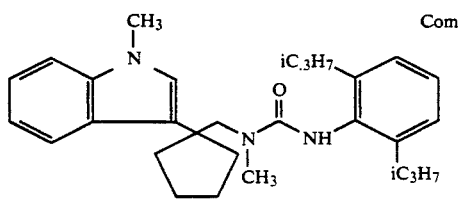
Compound No. 49

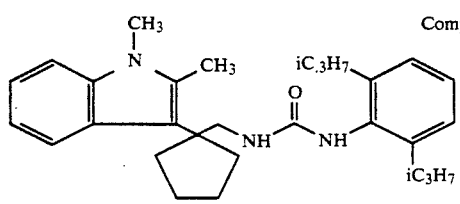
Compound No. 50

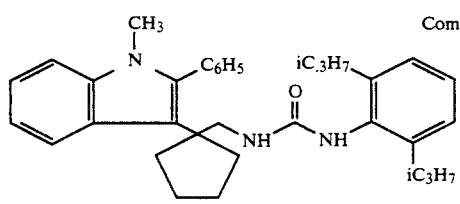
Compound No. 51

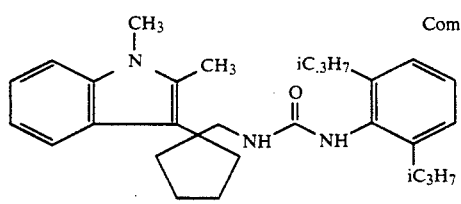
Compound No. 52

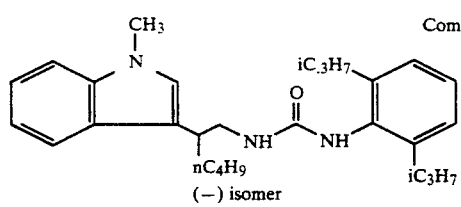
Compound No. 53
(−) isomer

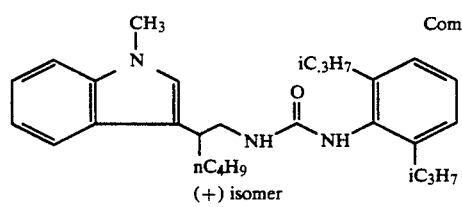
Compound No. 54
(+) isomer

We claim:
1. A compound selected from the compounds of the following formula I

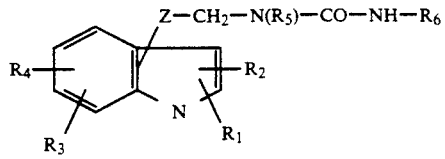

in which
$R_1$ and $R_2$, which may be located at position 1-, 2- or 3- of the indole ring-system, are independently selected from hydrogen, linear alkyl having 1 to 12 carbon atoms, branched alkyl having 3 to 5 carbon atoms, $C_3$-$C_6$ alkenyl, $C_3$-$C_8$ cycloalkyl, N-($C_1$-$C_5$ alkyl)amino($C_1$-$C_5$ alkyl), and N,N-di($C_1$-$C_5$ alkyl)amino($C_1$-$C_5$ alkyl), or one of the substituents $R_1$ or $R_2$ represents 2-pyridyl(or 3- or 4-pyridyl)-methyl and the other hydrogen, on the understanding that when the nitrogen atom of the indole ring-system is not substituted with any of the groups $R_1$, $R_2$ or —Z—$CH_2$—N($R_5$)CONHR$_6$, it is substituted with hydrogen, $R_3$ and $R_4$, which may be located at position 4-, 5-, 6- or 7- of the indole ring-system, are independently selected from hydrogen, halogen, $C_1$-$C_5$ alkyl, $C_1$-$C_5$ alkoxy and $C_1$-$C_5$ alkylthio,
or one of the substituents $R_3$ or $R_4$ is hydrogen and the other substituent is selected from trifluoromethyl, nitro, N-($C_1$-$C_5$ alkyl)amino and N,N-di($C_1$-$C_5$ alkyl)amino, or three of the substituents, $R_1$, $R_2$, $R_3$ or $R_4$ have the meanings which have just been defined and the fourth represents a radical of the following formula 2:

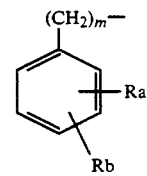

in which m can take the values 0, 1 or 2 and the substituents Ra and Rb independently are selected from halogen, $C_1$-$C_5$ alkyl, $C_1$-$C_5$ alkoxy and $C_1$-$C_5$ alkylthio, $R_5$ is selected from linear alkyl having 1 to 12 carbon atoms, or branched alkyl having 3 to 5 carbon atoms, $C_3$-$C_8$ cycloalkyl and a radical of formula 2, in which m has the value 1 and Ra and Rb have the meaning defined above,
$R_6$ is selected from $C_1$-$C_5$ alkyl and a radical of the following formula 3:

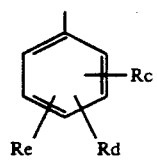

in which Rc, Rd and Re independently are selected from hydrogen, halogen, $C_1$-$C_5$ alkyl, $C_1$-$C_5$ alkoxy and $C_2$-$C_5$ alkylthio, or two of the substituents Rc, Rd and Re can have the meanings which have just been defined and the third is trifluoromethyl, and a pyrimidinyl group optionally substituted with one to three substituents selected from halogen, $C_1$-$C_5$ alkyl and $C_1$-$C_5$ alkoxy, Z, which can be attached to positions 1-, 2-, 3-, 4-, 5-, 6- or 7- of the indole ring-system, is selected from the bivalent radicals of formula —CH═CH—C($R_7R_8$)— and —($CH_2$)$_n$C—($R_7R_8$)—($CH_2$)$_p$, in which n and p are two integers which can take the values 0, 1 and 2, on condition that their sum (n+p) is not greater than 2, $R_7$ and $R_8$ are independently selected from hydrogen, linear alkyl having 1 to 12 carbon atoms, branched alkyl having 3 to 5 carbon atoms, $C_3$-$C_6$ alkenyl, $C_3$-$C_8$ cycloalkyl, N-($C_1$-$C_5$ alkyl)amino, N,N-di($C_1$-$C_5$ alkyl)amino, N-($C_1$-$C_5$ alkyl)amino($C_1$-$C_5$ alkyl), N,N-di($C_1$-$C_5$ alkyl)amino($C_1$-$C_5$ alkyl) and a group of formula 2 in which m can take the values 0 or 1 and Ra and Rb have the meanings defined above, $R_7$ and $R_8$ together can also form a polymethylene chain —($CH_2$)$_q$- in which q can take the values 3 to 8 and which is liable, where appropriate, when q is not less than 5, of containing a double bond, $R_7$ and $R_8$ together can also form the chains:
—$CH_2$—O—($CH_2$)$_2$—, —($CH_2$)$_2$—O—($CH_2$)$_2$—, —$CH_2$—S—($CH_2$)$_2$—, —($CH_2$)$_2$—S—($CH_2$)$_2$—, —$CH_2$—N($R_9$)—($CH_2$)$_2$— or —($CH_2$)$_2$—N($R_9$)—($CH_2$)$_2$—, $R_5$, $R_7$ and $R_8$ can also, when they represent a $C_3$—$C_8$ cycloalkyl radical, contain a double bond, and $R_9$ represents $C_1$-$C_5$ alkyl.

2. A compound as claimed in claim 1, in which the substituents $R_3$ and $R_4$ are selected from hydrogen, halogen, $C_1$-$C_5$ alkyl, N-($C_1$-$C_5$ alkyl)amino, N,N-di($C_1$-$C_5$ alkyl)amino, $C_1$-$C_5$ alkoxy, $R_5$ is selected from hydrogen, linear $C_1$-$C_{12}$ alkyl and a group of the following formula 2:

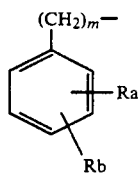

in which
m=1 and the substituents Ra and Rb independently are selected from hydrogen, halogen, $C_1$-$C_5$ alkyl, $C_1$-$C_5$ alkoxy and $C_1$-$C_5$ alkylthio and $R_6$ is a group of formula 3:

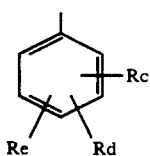

in which Rc, Rd and Re independently are selected from hydrogen, halogen, $C_1$-$C_5$ alkyl, $C_1$-$C_5$ alkoxy and $C_1$-$C_5$ alkylthio, or two of the substituents Rc, Rd and Re can have the meanings which have just been defined and the third is trifluoromethyl.

3. A compound as claimed in claim 1, selected from the following compounds:

$N^1$-(2,6-Diisopropylphenyl)-$N^2$-[1-(methyl-3-indolyl)cyclopentylmethyl]urea, $N^1$-[1-(1-Indolyl)-cyclopentylmethyl]-$N^2$-(2,6-diisopropylphenyl)urea, $N^1$-(2,6-Diisopropylphenyl)-$N^2$-{3-[1-(1-methyl-3-indolyl)cyclopentyl]propyl}-urea, $N^1$-(2,6-Diisopropylphenyl)-$N^2$-{2-[1-(1-methyl-3-indolyl)cyclopentyl]ethyl}urea, $N^1$-Benzyl-$N^2$-(2,6-diisopropylphenyl)-$N^1$-[1-(1-methyl-3-indolyl)cyclopentylmethyl]urea, $N^2$-[1-(1-Methyl-3-indolyl)cyclopentylmethyl]-$N^1$-phenyl)urea, $N^1$-[2-(3-Indolyl)ethyl]-$N^2$-(2,6-diisopropylphenyl)urea, $N^1$-(2,4-Difluorophenyl)-$N^2$-[1-(1-methyl-3-indolyl)cyclopentylmethyl]urea, $N^1$-(2,6-Diisopropylphenyl)-$N^2$-[3-methyl-2-(1-methyl-3-indolyl)butyl]-urea, $N^1$-tert-Butyl-$N^2$-[1-(1-methyl-3-indolyl)cyclopentylmethyl]urea, $N^1$-(2,6-Diisopropylphenyl)-$N^2$-[2-(1-methyl-3-indolyl)propyl]urea, $N^1$-[1-(1-Benzyl-3-indolyl)cyclopentylmethyl]-$N^2$-(2,6-diisopropylphenyl)urea, $N^1$-[1-(1-Ethyl-3-indolyl)cyclopentyl-methyl]$N^2$-(2,6-diisopropylphenyl)urea, $N^1$-(2,6-Diisopropylphenyl)-$N^2$-[2-(1-methyl-3-indolyl)butyl]urea, $N^1$-(2,6-Diisopropylphenyl)-$N^2$-[1-(1,5-dimethyl-3-indolyl)cyclopentylmethyl]urea, $N^1$-(2,6-Diisopropylphenyl)-$N^2$-[1-(1-methyl-3-indolyl)cyclohexylmethyl urea, $N^1$-[2-Ethyl-2-(1-methyl-3-indolyl)-2-butyl]-$N^2$-(2,6-diisopropylphenyl)urea, $N^1$-(2,6-Diisopropylphenyl)-$N^2$-[2-methyl-2-(1-methyl-3-indolyl)propyl]urea, $N^1$-[1-(1-Isopropyl-3-indolyl)cyclopentylmethyl]-$N^2$-(2,6-diisopropylphenyl)urea, $N^1$-[1-(1-Allyl-3-indolyl)cyclopentylmethyl]-$N^2$-(2,6-diisopropylphenyl)urea, $N^2$-(2,6-Diisopropylphenyl)-$N^2$[2-(1-methyl-3-indolyl)-2-phenylethyl]urea, $N^1$-[2-Allyl-2-(1-methyl-3-indolyl)-4-pentenyl]-$N^2$-(2,6-diisopropylphenyl)urea, $N^1$-(2,6-Diisopropylphenyl)-$N^2$-[1-(1-phenyl-3-indolyl)cyclopentylmethyl]urea, $N^1$-(2,6-Diisopropylphenyl)-$N^2$-[1-(1-methyl-3-indolyl)cyclobutylmethyl]urea, $N^1$-[2-Butyl-2-(1-methyl-3-indolyl)hexyl]-$N^2$-(2,6-diisopropylphenyl)urea, $N^1$-(2,6-Diisopropylphenyl)-$N^2$-[2-(1-methyl-3-indolyl)-4-pentenyl]-urea, $N^1$-[1-(1-Heptyl-3-indolyl)cyclopentyl-methyl]-$N^2$-)2,6-diisopropylphenyl)urea, $N^1$-[1-(1-Butyl-3-indolyl)cyclopentylmethyl]-$N^2$-(2,6-diisopropylphenyl)urea, $N^1$-(2,6-Diisopropylphenyl)-$N^2$-[2-(1-methyl-3-indolyl)-hexyl]-urea, $N^1$-(2,6-Diisopropylphenyl)-$N^2$-[2-(1-methyl-3-indolyl)nonyl]urea, $N^1$-(2,6-Diisopropylphenyl)-$N^2$-[4,4-dimethyl-2-(1-methyl-3-indolyl)pentyl]urea, $N^1$-(2,6-Diisopropylphenyl)-$N^2$-[2-(1-methyl-3-indolyl)-3-phenylpropyl]-urea, $N^1$-(2,6-Dichlorophenyl)-$N^2$-[1-(1-methyl-3-indolyl)-cyclopentylmethyl]urea, $N^1$-(2,6-Diisopropylphenyl)-$N^2$-[1-(1-methyl-3-indolyl)cycloheptylmethyl]urea, $N^1$-(2,6-Diisopropylphenyl)-$N^2$-[1-(1-methyl-3-indolyl)tetrahydro-4-pyranylmethyl]urea, $N^1$-(2,6-Diethylphenyl)-$N^2$-[1-(1-methyl-3-indolyl)cyclopentylmethyl]urea, $N^1$-(2,6-Diisopropylphenyl)-$N^2$-{1-[1-(2-dimethylaminoethyl)-3-indolyl]-cyclopentylmethyl}urea, $N^1$-{1-[1-(4-Fluorobenzyl)-3-indolyl]-cyclopentylmethyl}-$N^2$-(2,6-diisopropylphenyl)-urea, $N^1$-(2,4,6-Trimethoxyphenyl)-$N^2$-[1-(1-methyl-3-indolyl)cyclopentylmethyl]urea, $N^1$-(4,6-Dimethoxy-5-pyrimidinyl)-$N^2$-[1-(1-methyl-3-indolyl)cyclopentylmethyl]-urea, $N^1$-(2,6-Diisopropylphenyl)-$N^2$-[1-(5-methoxy-1-methyl-3-indolyl)cyclopentylmethyl]urea, $N^1$-(2,6-Diisopropylphenyl)-$N^2$-[4-dimethylamino-2-(1-methyl-3-indolyl)-butyl]urea, $N^1$-(2,6-Diisopropylphenyl)-$N^2$-[5-methyl-2-(1-methyl-3-indolyl]-4-hexenyl]urea, $N^1$-(2,6-Diisopropoxyphenyl)-$N^2$-[1-(1-methyl-3-indolyl)cyclopentylmethyl]urea, $N^1$-(2,6-Diisopropylphenyl)-$N^2$-{1-[1-(3-pyridylmethyl)-3-indolyl]cyclopentylmethyl}urea, $N^1$-Benzyl-$N^1$-[1-(1-methyl-3-indolyl)-cyclopentylmethyl]-$N^2$-(2,6-dimethylphenyl]urea, $N^1$-benzyl-$N^2$-(2,6-dichlorophenyl)-$N^1$-[1-(1-methyl-3-indolyl)cyclopentylmethyl]urea, $N^1$-Benzyl-$N^2$-(2,4-difluorophenyl)-$N^1$-[1-(1-methyl-3-indolyl)-cyclopentylmethyl]urea, $N^2$-(2,6-Diisopropylphenyl)-$N^1$-methyl-$N^1$-[1-(1-methyl-3-indolyl)cyclopentylmethyl]urea, $N^1$-(2,6-Diisopropylphenyl)-$N^2$-[1-(1,2-dimethyl-3-indolyl)-cyclopentylmethyl]urea, $N^1$-(2,6-Diisopropylphenyl)-$N^2$-[1-(1-methyl-2-pentyl-3-indolyl)cyclopentylmethyl]urea, $N^1$-(2,6-Diisopropylphenyl)-$N^2$-[1-(1,3-dimethyl-2-indolyl)-cyclopentylmethyl]urea, (-)-$N^1$-(2,6-Diisopropylphenyl)-$N^2$-[2-(1-methyl-3-indolyl)hexyl]urea, (+)-$N^1$-(2,6-Diisopropylphenyl)-$N^2$-[2-(1-methyl-3-indolyl)-hexyl]urea.

4. A therapeutic composition having an antihyperlipidaemic activity, comprising an effective amount of compound of formula 1 as claimed in claim 1, in admixture with a pharmaceutically acceptable excipient.

5. Pharmaceutical composition as claimed in claim 4, in the form of a dosage unit in which each dosage unit contains 10 to 500 mg of compound of formula 1 in admixture with a pharmaceutically acceptable excipient.

6. A method for the treatment of hyperlipidaemia which comprises administering to a human in need thereof an effective amount of a compound as claimed in claim 1.

7. A method for the treatment of atherosclerosis which comprises administering to a human in need thereof an effective amount of a compound as claimed in claim 1.

8. A method for the treatment of hyperglycaemia which comprises administering to a human in need thereof an effective amount of a compound as claimed in claim 1.

* * * * *